(12) United States Patent
Kaplan

(10) Patent No.: US 7,833,523 B2
(45) Date of Patent: Nov. 16, 2010

(54) COMPOSITIONS AND METHODS FOR ENZYMATIC DETACHMENT OF BACTERIAL AND FUNGAL BIOFILMS

(75) Inventor: Jeffrey B. Kaplan, Monsey, NY (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 522 days.

(21) Appl. No.: 11/938,617

(22) Filed: Nov. 12, 2007

(65) Prior Publication Data

US 2008/0181925 A1 Jul. 31, 2008

Related U.S. Application Data

(63) Continuation of application No. 10/538,902, filed as application No. PCT/US03/34683 on Oct. 31, 2003, now Pat. No. 7,294,497.

(60) Provisional application No. 60/435,817, filed on Dec. 20, 2002.

(51) Int. Cl.
*A61K 38/46* (2006.01)
*C12N 9/24* (2006.01)

(52) U.S. Cl. ..................... 424/94.6; 435/200
(58) Field of Classification Search ................ 424/94.6; 435/200
See application file for complete search history.

(56) References Cited

U.S. PATENT DOCUMENTS 5,238,843 A 8/1993 Carpenter et al.
7,064,105 B2 6/2006 Joullie et al.

FOREIGN PATENT DOCUMENTS

JP 3-231999 10/1991
WO WO 98/50512 11/1998

OTHER PUBLICATIONS

Kaplan, J.B., et al., "Actinobacillus actinomycetemcomitans DspB (dspB) gene, partial cds," http://www.ncbi.nlm.nih.gov/sviewer/viewer.fcgi?30420959:NCBI:5172251, Database GenBank [online], Accession No. AY228551, Aug. 4, 2003.
Hornbeck et al., "Enzyme-Linked Immunosorbent Assays (ELISA)". In: Current Protocols in Molecular Biology Jul. 1991, pp. 11.2.1-22.
Gayle et al., "Identification of Regions in Interleukin-1 Alpha Important for Activity". *J Biol Chem.* Oct. 15, 1993; 268(29):22105-11.
Grant et al., "Synthetic Peptides for Production of Antibodies that Recognize Intact Proteins". In: Current Protocols in Molecular Biology Print Publication Date: Jul. 2002, pp. 11.16.1-19.
Whisstock et al., "Prediction of Protein Function from Protein Sequence and Structure". *Q Rev Biophys.* Aug. 2003; 36(3):307-40.
Office Action dated Jun. 2, 2010 in co-pending U.S. Appl. No. 11/833,705.
Office Action dated Nov. 25, 2009 in co-pending U.S. Appl. No. 11/833,705.
Clarke et al., 1995, "Cloning and Expression of the β-N-Acetylglucosaminidase Gene from *Streptococcus pneumoniae*", *J. of. Biological Chemistry*, 270(15):8805-8814.
Graham et al., 1968, "Molecular Cloning of the cDNA which Encodes β-N-Acetylhexosaminidase A from *Dictyostelium discoideum*", *J of. Biological Chemistry*, 263(32): 16823-16829.
Kaplan et al., 2003, "Detachment of *Actinobacillus actinomycetemcomitans* Biofilm Cells by an Endogenous β-Hexosaminidase Activity", *J. Bacteriology*, 185(16):4693-4698.
Kaplan et al., 2001, "Structural and genetic analyses of O polysaccharide from *Actinobacillus actinomycetemcomitans* serotype f," *Infect. Immun.* 69: 5375-5384.
Kaplan et al., 2002, "Biofilm dispersal of *Neisseria subflava* and other phylogenetically diverse oral bacteria," *Appl. Environ. Microbiol.* 68(10): 4943-4950.
Kaplan et al., 2003, "Biofilm growth and detachment of *Actinobacillus actinomycetemcomitans*", *J. Bacteriol.*, 185(4):1399-1404.
Somerville et al., 1993, "Sequence analysis of the β-N-Acetylglucosaminidase gene of *Vibrio vulnificus*: Evidence for a common evolutionary origin of hexosaminidases", *Proc. Natl. Acad. Sci. USA*, 90:6751-6755.
Donlan, "Biofilms: Microbial Life on Surfaces", *Emerging Infectious Diseases*, 8(9):881-890 (2002).
Database EMBL, "Mus musculus BAC clone RP24-363G13 from chromosome 3, complete sequence", Accession No. AC127237 (Jul. 18, 2002).
Database EMBL, "Streptococcus suis FlpS (flpS) gene, complete cds; arginine deiminase operon operon, complete sequence; ArcD (arcD), ArcT (arcT), ArcH (arcH), and ArgR (argR) genes, compete cds; and unknown genes", Accession No. AF546864 (Dec. 4, 2002).

*Primary Examiner*—Tekchand Saidha
(74) *Attorney, Agent, or Firm*—Brian R. Dorn; Merchant & Gould P.C.

(57) ABSTRACT

Isolated nucleic acid sequences and amino acid sequences for soluble, β-N-acetylglucosaminidase or active fragments or variants thereof which promote detachment of bacterial cells from a biofilm are provided. An isolated mutant bacteria which forms biofilm colonies which tightly adhere to surface but which are unable to release cells into the medium or spread over the surface is also provided. In additions, methods are described for modulating detachment of bacterial cells from biofilm by mutating soluble, β-N-acetylglucosaminidase or altering its expression or activity are also provided. Also provided are compositions, methods and devices for preventing, inhibiting and treating bacterial infections.

13 Claims, 1 Drawing Sheet

FIGURE 1

```
SEQ ID NO:2   DHENYAIESHLLNQRAENAVQGKDGIYINPYTGKPFLSYRQLDDIKAYAKAKGIELIPEL  60
SEQ ID NO:6   DHENYAIESHLLNQRAENAVQGKDGIYINPYTGKPFLSYRQLDDIKAYAKAKGIELIPEL  60
SEQ ID NO:8   DHENYALESRLLNQRAENAILNKNGIYINPYTNKPFLSYQQLDDIKAYAKLKGIELIPEL  60
SEQ ID NO:4   DHENYALESSYLEQREENAVE-KNGTYFNPKTNKPFLTYKQLNEIIYYAKERNIEIVPEV  59
SEQ ID NO:10  DHENYALESSYLEQREENATE-KNGTYFNPKTNKPFLTYKQLNEIIYYAKERNIEIVPEV  59
              ****** ** *  *:*** * :** *:** *:***:*:** :*   ***:  **:**:

SEQ ID NO:2   DSPNHMTAIFKLVQKDRGVKYLQGLKSRQVDDEIDITNADSITFMQSLMSEVIDIFGDTS 120
SEQ ID NO:6   DSPNHMTAIFKLVQKDRGIKYLQGLKSRQVDDEIDITNADSIAFMQSLMSEVIDIFGDTS 120
SEQ ID NO:8   DSPNHMTAIFTLLKKEKGKNYLQSLKSPQNDEEISITNPDSIAFMQSLLTEVIHTFGDST 120
SEQ ID NO:4   DSPNHMTAIFDLLTLKHGKEYVKGLKSPYLAEEIDINNPEAVEIIKTLIGEVIYIFGHSS 119
SEQ ID NO:10  DSPNHMTAIFDLLTLKHGKEYVKGLKSPYLAEEIDINNPEAVEVIKTLIGEVIYIFGHSS 119
              ********** *:   : * :*  *** :  :**.*  ** .: :  ::*** ***::

SEQ ID NO:2   QHFHIGGDEFGYSVESNHEFITYANKLSYFLEKKGLKTRMWNDGLIKNTFEQINPNIEIT 180
SEQ ID NO:6   QHFHIGGDEFGYSVESNHEFITYANKLSYFLEKKGLKTRMWNDGLIKSTFEQINPNIEIT 180
SEQ ID NO:8   KHFHIGGDEFGYDENSNHEFITYANKLADFLREKGLKTRIWNDGLIKNTIDQLNPNIEIT 180
SEQ ID NO:4   RHFHIGGDEFSYAVENNHEFIRYVNTLNDFINNDGLITRIWNDGLIKNNLELNRNIEIT 179
SEQ ID NO:10  RHFHIGGDEFSYAVENNHEFIRYVNTLNDFINSKGLITRVWNDGLIKNNLSELNKNIEIT 179
              :********.*  *.****** * * *: *:  ***.*:*******.   ::* ****

SEQ ID NO:2   YWSYDG 186
SEQ ID NO:6   YWSYDG 186
SEQ ID NO:8   YWSYDG 186
SEQ ID NO:4   YWSYDG 185
SEQ ID NO:10  YWSYDG 185
              ******
```

COMPOSITIONS AND METHODS FOR ENZYMATIC DETACHMENT OF BACTERIAL AND FUNGAL BIOFILMS

CROSS-REFERENCE TO RELATED APPLICATIONS

This application is a continuation of U.S. application Ser. No. 10/538,902, now U.S. Pat. No. 7,294,497, filed May 15, 2006, which is a national stage entry under 35 U.S.C. §371 of PCT/US03/34683, filed Oct. 31, 2003, which claims the benefit of priority from U.S. Provisional Application Ser. No. 60/435,817, filed Dec. 20, 2002, which is herein incorporated by reference in its entirety.

STATEMENT OF RIGHTS TO DISCLOSURES MADE UNDER FEDERALLY SPONSORED RESEARCH AND DEVELOPMENT

The work performed during the development of this disclosure utilized intramural support from the National Institutes of Health. The United States government may have certain rights in the disclosure.

FIELD OF THE INVENTION

The present invention provides isolated nucleic acid sequences and amino acid sequences encoded thereby for the protein, soluble, β-N-acetylglucosaminidase or dispersin B, and active fragments and variants thereof, which promote detachment of bacterial cells from biofilms. Vectors comprising the nucleic acid sequences as well as host cells expressing the dispersin B protein or active fragments or variants thereof are also provided. A biofilm detachment mutant of *A. actinomycetemcomitans* is also described. The nucleic acid and amino acid sequences of the present invention are useful in methods for modulating detachment of bacterial or fungal cells from biofilms as well as in methods for identifying agents which modulate detachment of bacterial or fungal cells from biofilms. Thus, these nucleic acid and amino acid sequences and agents are expected to be useful in the prevention and treatment of bacterial or fungal infections and in disinfectant and antiseptic solutions.

BACKGROUND OF THE INVENTION

Biofilms are populations of bacteria or fungi growing attached to an inert or living surface. Mounting evidence has shown that biofilms constitute a significant threat to human health. The Public Health Service estimates that biofilms are responsible for more than 80% of bacterial infections in humans (National Institutes of Health, 1998 RFA# DE-98-006). Examples of diseases caused by biofilms include dental caries, periodontitis, cystic fibrosis pneumonia, native valve endocarditis, and otitis media (Costerton et al. Science 1999 284:1318-1322), as well as infection of various medical devices such as urinary catheters, mechanical heart valves, cardiac pacemakers, prosthetic joints, and contact lenses (Donlan, R. M. 2001 Emerging Infect. Dis. 7:277-281). Fungi also form biofilms of clinical significance, for example *Candida* infections. Biofilm infections afflict tens of millions of patients in the U.S. annually and require a significant expenditure of health care dollars (Costerton et al. Science 1999 284:1318-1322). Bacteria growing in biofilms exhibit increased resistance to antimicrobial agents and are nearly impossible to eradicate. New methods for treating biofilm infections are needed.

Bacteria in a biofilm are enmeshed in an extracellular polysaccharide (EPS) substance that holds the bacteria together in a mass, and firmly attaches the bacterial mass to the underlying surface. Previous studies have demonstrated that enzymes that degrade EPS are capable of causing the detachment of cells from biofilms. For example, over expression of alginate lyase, an enzyme that catalyzes the degradation of the EPS alginate, causes colonies of *Pseudomonas aeruginosa* to become less adherent to surfaces (Boyd, A. and Chakrabarty, A. M. Appl. Environ. Microbiol. 1994 60:2355-2359). Alginate lyase has been suggested for use in treating *P. aeruginosa* infections in the lungs of cystic fibrosis patients (Mrsny et al. Pulm. Pharmacol. 1994 7:357-366). A similar polysaccharide lyase has been shown to be produced by *P. fluorescens* (Allison et al. FEMS Microbiol. Lett. 1998 167:179-184). Two other EPS-degrading enzymes, endo-β-1,4-mannanase from the plant pathogen *Xanthomonas campestris* (Dow et al. Proc. Nat. Acad. Sci. USA 2003 100:10995-11000) and disaggretase from the methanogenic archaebacterium *Methanosarcina mazei* (Liu et al. Appl. Environ. Microbiol. 1985 49:608-613), have also been shown to cause biofilm cell detachment. In the case of *X. campestris*, production of the EPS-degrading enzyme was required for full virulence of the bacteria in plants. Detachment of cells from biofilm colonies of the dental pathogen *Streptococcus mutans* was shown to be caused by an unidentified endogenous enzymatic activity (Lee et al. Infect. Immun. 1996 64:1035-1038). A complex mixture of polysaccharide-hydrolyzing enzymes was shown to remove biofilms from steel and polypropylene substrata (Johansen et al. Appl. Environ. Microbiol. 1997 63:3724-3728). These findings indicate that EPS-degrading enzymes can potentially be used as agents to remove biofilms from surfaces.

Although enzymes are commonly used to remove biofilms in industrial environments, no studies have investigated the potential use of enzymes as agents for the removal of biofilms in clinical environments. Of particular concern in the clinic are biofilm infections of indwelling medical devices, especially intravascular catheters. Catheter infections are common in hospitalized patients and are associated with high levels of morbidity and mortality. A promising new approach to treating these infections is the use of catheters that are coated or impregnated with antimicrobial agents such as antibiotics (Schierholz et al. J. Antimicrobial. Chemother. 2000 46:45-50), silver (Bechert et al. Infection 1999 27:S24-S29), and peptide quorum-sensing inhibitors (Balaban et al. J. Infect. Dis. 2003 187:625-630). Numerous studies have demonstrated that medical devices with antimicrobial activity decrease the risk of bacterial colonization and infection (Tcholakian, R. K. and Raad, I. I. Antimicrob. Agents Chemother. 2001 45:1990-1993).

The present invention provides isolated proteins and active fragments and variants thereof and nucleic acid sequences encoding such proteins and active fragments and variants thereof involved in detachment of bacterial cells. Methods for modulating detachment of biofilm cells of bacteria or fungi and identifying agents which modulate bacterial or fungal detachment via these proteins and active fragments and variants thereof and/or nucleic acid sequences are also provided.

SUMMARY OF THE INVENTION

An object of the present invention is to provide isolated proteins and active fragments and variants thereof which promote detachment of bacterial or fungal cells from a biofilm. The isolated proteins are referred to herein as soluble, β-N-acetylglucosaminidase or dispersin B.

Another object of the present invention is to provide isolated nucleic acid sequences encoding soluble, β-N-acetylglucosaminidase and active fragments and variants thereof as well as vectors comprising these sequences and host cells expressing the vectors.

Another object of the present invention is to provide methods for modulating detachment of bacterial or fungal cells from biofilms. In one embodiment the method comprises mutating the bacterial cells to inhibit detachment of bacterial cells from biofilms. In another embodiment, the method comprises increasing expression and/or levels of soluble, β-N-acetylglucosaminidase or active fragments or variants thereof in the bacterial or fungal cells so that detachment is increased. In yet another embodiment, the method comprises decreasing expression and/or levels of soluble, β-N-acetylglucosaminidase or active fragments or variants thereof or inhibiting activity of soluble, β-N-acetylglucosaminidase or active fragments or variants thereof so that detachment of bacterial cells is decreased.

Another object of the present invention is to provide an isolated mutant of *Actinobacillus actinomycetemcomitans* which forms biofilm colonies which tightly adhere to surface but which are unable to release cells into the medium or spread over the surface.

Another object of the present invention is to provide a method for identifying agents which modulate detachment of bacterial or fungal cells from biofilms which comprises assessing the ability of an agent to modulate activity and/or levels and/or expression of soluble, β-N-acetylglucosaminidase.

Another object of the present invention is to provide compositions and methods for using these compositions to prevent the dissemination of infectious bacteria via administration of an agent which inhibits soluble, β-N-acetylglucosaminidase expression and/or activity in the bacterial cells.

Another object of the present invention is to provide compositions and methods for preventing or inhibiting attachment of infectious bacteria or fungi to a surface or removing infectious bacteria or fungi from a surface which comprises treating the surface with soluble, β-N-acetylglucosaminidase, or an active fragment or variant thereof.

Yet another object of the present invention is to provide PCR primer pairs and kits comprising such primer pairs that can be used to identify additional bacterial species with homologues of soluble, β-N-acetylglucosaminidase.

BRIEF DESCRIPTION OF THE FIGURE

FIG. 1 provides a clustal alignment of exemplary dispersin B orthologs of the present invention from *A. actinomycetemcomitans* strain CU1000N (SEQ ID NO:2), *A. actinomycetemcomitans* strain IDH781 (SEQ ID NO:6), *Haemophilus aphrophilus* strain NJ8700 (SEQ ID NO:8), *A. ligniersii* strain 19393 (SEQ ID NO:4), and *A. pleuropneumoniae* strain IA5 (SEQ ID NO:10).

DETAILED DESCRIPTION OF THE INVENTION

The small, gram-negative coccobacillus *Actinobacillus actinomycetemcomitans* is a common inhabitant of the human oral cavity (King, E. O. and Tatum, H. W. J. Infect. Dis. 1962 111:85-94). *A. actinomycetemcomitans* has been implicated as the causative agent of localized juvenile periodontitis, a severe and rapid form of periodontal disease that affects adolescents (Zambon, J. J. J. Clin. Periodontol 1985 12:1-20). *A. actinomycetemcomitans* can also enter the sub-mucosa and cause infective endocarditis and other non-oral infections (Kaplan et al. Rev. Infect. Dis. 1989 11:46-63).

When cultured in broth, fresh clinical isolates of *A. actinomycetemcomitans* form tenacious biofilms on surfaces such as glass, plastic and saliva-coated hydroxyapatite (Fine et al. Arch. Oral. Biol. 1999 44:1063-1076; Fine et al. Microbiol. 1999 145:1335-1347; Fine et al. Arch. Oral Biol. 2001 46:1065-1078; Haase et al. Infect. Immun. 1999 67:2901-2908; Inouye et al. FEMS Microbiol. Lett. 1990 69:13-18; Kachlany et al. J. Bacteriol. 2000 182:6169-6176; Kachlany et al. Mol. Microbiol. 2001 40:542-554; Kagermeier, A. S., and London, J. Infect. Immun. 1985 47:654-658; Kaplan, J. B., and Fine, D. H. Appl. Environ. Microbiol. 2002 68:4943-4950; King, E. O. and Tatum, H. W. J. Infect. Dis. 1962 111:85-94; Rosan et al. Oral. Microbiol. Immunol. 1988 3:58-63). Nearly all of the cells grow attached to the surface while the broth remains clear and is often sterile (Fine et al. Arch. Oral. Biol. 1999 44:1063-1076). The dense biofilm that forms on the surface is resistant to removal by agents such as detergents, proteases, heat, sonication and vortex agitation (Fine et al. Arch. Oral. Biol. 1999 44:1063-1076), and can be removed only by mechanical scraping. *A. actinomycetemcomitans* biofilm colonies exhibit increased resistance to antimicrobial agents when compared to cells grown in planktonic form (Fine et al. J. Clin. Periodontol. 2001 28:697-700).

Tight adherence has been shown to play an important role in the ability of *A. actinomycetemcomitans* to colonize the mouths of rats (Fine et al. Arch. Oral Biol. 2001 46:1065-1078.), and is believed to have an equally important role in its ability to colonize humans. The tight adherence to surfaces is dependent on the presence of long, bundled pili (fimbriae) that form on the surface of the cell (Inouye et al. FEMS Microbiol. Lett. 1990 69:13-18; Rosan et al. Oral. Microbiol. Immunol. 1988 3:58-63). Mutations in flp-1, which encodes the major pilin protein subunit, result in cells that fail to produce fimbriae or adhere to surfaces (Kachlany et al. Mol. Microbiol. 2001 40:542-554).

Biofilm colonies of *A. actinomycetemcomitans* have been shown to release cells into liquid medium which then attach to the surface of the culture vessel and form new colonies, enabling the biofilm to spread (Kaplan, J. B. and Fine D. H. Appl. Environ. Microbiol. 2002 68: 4943-4950.).

One aspect of the present invention relates to a mutant of *A. actinomycetemcomitans* that forms biofilm colonies which are tightly adherent to surfaces but which are unable to release cells into the medium or spread over the surface. The biofilm detachment mutant of *A. actinomycetemcomitans* is referred to herein as mutant JK1023. To produce the *A. actinomycetemcomitans* biofilm detachment mutant JK1023, the *A. actinomycetemcomitans* strain CU1000N was mutagenized with transposon IS903φkan. The mutant strain (designated JK1023) was then isolated. This mutant strain displays a colony morphology on agar that is rougher than the wild-type *A. actinomycetemcomitans* rough-colony phenotype (Fine et al. Microbiol. 1999 145:1335-1347; Haase et al. Infect. Immun. 1999 67:2901-2908; Inouye et al. FEMS Microbiol. Lett. 1990 69:13-18). JK1023 colonies had a hard texture and were extremely difficult to remove from the agar surface. When cultured in broth, strain JK1023 produced biofilm colonies which were similar in size and shape to those of the wild-type strain, but which failed to produce satellite colonies on the surface of the culture vessel. Adherence of JK1023 cells to polystyrene was equal to that of wild-type strain CU1000N as measured by a 96-well microtiter plate binding assay.

To demonstrate that biofilm colonies of mutant strain JK1023 of the present invention were deficient in biofilm cell detachment, biofilm colonies were grown for 24 hours on polystyrene rods suspended in broth in the wells of a 24-well microtiter plate. The amount of biofilm cell detachment was then quantified by staining the bacteria growing on the bottom of the well with crystal violet. Colonization at the bottom of the well results from cells that detach from the biofilm colonies growing on the polystyrene rod and fall to the bottom of the well. In this assay, biofilm colonies of strain JK1023 produced significantly less growth on the bottom of the well than the wild-type strain (P<0.01, unpaired two-tailed t test). These data indicate that mutant strain JK1023 exhibited a wild-type surface attachment phenotype but a decreased biofilm cell detachment phenotype when compared to the wild-type strain CU1000N.

DNA sequence analysis of the region surrounding the transposon insertion site of this mutant strain revealed the insertion to be in a 1,143 bp open reading frame designated herein as dspB. The dspB gene from strain CU1000 was predicted to encode a protein, referred to herein as dispersin B, having 381 amino acid residues with a molecular mass of 43.3 kDa. The 5' end of dspB contained a predicted signal peptide, suggesting that dispersin B may be a secreted protein.

In addition to *A. actinomycetemcomitans*, dspB nucleic acid sequences or fragments have also been isolated from *Actinobacillus pleuropneumonaie, Haemophilus aphrophilus* and *Actinobacillus ligniersii*. DspB is not present in the genomes of *Haemophilus influenzae, Pasteurella multicido, Mannheimia haemolytica, Actinobacillus equuli* and *Haemophilus ducreyi* among the strains that were tested.

Accordingly, another aspect of the present invention relates to nucleic acid sequences encoding dispersin B or active fragments and variants thereof as well as amino acid sequences of dispersin B and active fragments and variants thereof. Also encompassed by the present invention are vectors comprising these nucleic acid sequences as well as host cells comprising the vectors which express dispersin B or an active fragment thereof.

By the term "nucleic acid sequence" as used herein it is meant to include, but is not limited to, unmodified RNA or DNA or modified RNA or DNA. Thus, by nucleic acid sequence it is meant to be inclusive of single- and double-stranded DNA, DNA that is a mixture of single- and double-stranded regions, single- and double-stranded RNA, and RNA that is mixture of single- and double-stranded regions, hybrid molecules containing DNA and RNA that may be single-stranded or, more typically, double-stranded or a mixture of single- and double-stranded regions. Further, the DNA or RNA sequences of the present invention may comprise a modified backbone and/or modified bases. A variety of modifications to DNA and RNA are known in the art for multiple useful purposes. The term "nucleic acid sequence" as it is employed herein embraces such chemically, enzymatically or metabolically modified forms of nucleic acid sequences, as well as the chemical forms of DNA and RNA characteristic of viruses and cells, including simple and complex cells.

The DNA sequence of dspB from strain CU1000 was deposited into GenBank under accession no. AY228551 and released on Aug. 4, 2003. The nucleic acid sequence for this DNA is SEQ ID NO:1. Nucleic acid sequences encoding orthologs of dispersin B protein have been identified in *A. ligniersii* strain 19393, *A. actinomycetemcomitans* strain IDH781, *Haemophilus aphrophilus* strain NJ8700 and *A. pleuropneumoniae* strain IA5 and are depicted in SEQ ID NO:3, 5, 7 and 9, respectively. Accordingly, preferred isolated nucleic acid sequences of the present invention comprise SEQ ID NO:1, 3, 5, 7 or 9.

Also included within the present invention are allelic variants of the exemplified dspB nucleic acid sequences of SEQ ID NO:1, 3, 5 7 or 9 encoding proteins with similar enzymatic activities to dispersin B and nucleic acid sequences with substantial percent sequence identity to the exemplified dspB nucleic acid sequences of SEQ ID NO: 1, 3, 5, 7 or 9 encoding proteins with similar enzymatic activities.

By the term "allelic variant" as used herein it is meant one of two or more alternative naturally occurring forms of a gene, each of which comprises a unique nucleic acid sequence. Allelic variants encompassed by the present invention encode proteins with similar or identical enzymatic activities.

The term "percent sequence identity" as used herein with respect to nucleic acid sequences refers to the residues in two nucleic acid sequences which are the same when aligned for maximum correspondence. The length of sequence identity comparison is preferably over a length of at least about 9 contiguous nucleotides, more preferably about 18 contiguous nucleotides, and even more preferably at least about 30 to 50 contiguous nucleotides or more. Various algorithms well known in the art are available for measuring nucleic acid sequence identity. Examples include, but are not limited to, FASTA (including FASTA2 and FASTA3), Gap and Bestfit, which are programs in Wisconsin Package Version 10.0, Genetics Computer Group (GCG), Madison, Wis.

By "substantial percent sequence identity" when referring to a nucleic acid sequence or fragment thereof, of the present invention, it is meant that when optimally aligned with appropriate nucleotide insertions or deletions with another nucleic acid (or its complementary strand), at least about 50% of the nucleotide bases as measured by any well known algorithm of sequence identity, such as FASTA, BLAST or Gap are the same. For purposes of the present invention, more preferably, at least about 60% to 70%, even more preferably 80% to 90%, and most preferably at least about 95-98% of the nucleotide bases, as measured by any well known algorithm of sequence identity, such as FASTA, BLAST or Gap, are identical.

Nucleic acid sequences sharing substantial percent sequence identity and encoding proteins with similar functional activity are referred to herein as orthologues.

Deduced amino acid sequences of dispersin B and exemplary orthologues thereof are shown in FIG. 1. Specifically, the amino acid sequence of dispersin B of *A. actinomycetemcomitans* strain CU1000N (SEQ ID NO:2), and orthologs of dispersin B from *A. actinomycetemcomitans* strain IDH781 (SEQ ID NO:6), *Haemophilus aphrophilus* strain NJ8700 (SEQ ID NO:8), *A. ligniersii* strain 19393 (SEQ ID NO:4), and *A. pleuropneumoniae* strain IA5 (SEQ ID NO:10) are shown.

There are similarities between the amino acid sequence of dispersin B and these orthologs and the consensus sequence of the family 20 glycosyl hydrolase. More specifically, amino acid residues 40 to 297 of the predicted dispersin B protein sequence are homologous to the catalytic domain of the family 20 glycosyl hydrolases (NCBI Conserved Domain Database accession Number pfam00728). This family of enzymes includes bacterial chitinases, chitobiases and lacto-N-biosidases (Sano et al. J. Biol. Chem. 1993 268:18560-18566; Tews et al. Gene 1996 170:63-67; Tsujibo et al. Biochim. Biophys. Acta 1998 1425:437-440.), and eukaryotic hexosaminidases (Graham et al. J. Biol. Chem. 1988 263:16823-16829). A protein related to *A. actinomycetemcomitans* dispersin B is lacto-N-biosidase of *Lactococcus lactis* (GenBank accession no. AAK05592), which displays 28% identity over 281 amino acid residues not counting gaps and terminal extensions. Similarity between dispersin B and lacto-N-biosidases is high in the regions surrounding Arg47 and the acidic amino acid pair Asp202 and Glu203. These residues have been shown to participate in substrate binding and catalysis in other family 20 glycosyl hydrolases (Mark et al. J. Biol. Chem. 2001 276:10330-10337; Mark et al. J. Biol. Chem. 1998 273:19618-19624; Prag et al. J. Mol. Biol. 2000 300:611-617). The C-terminal half of dispersin B contained three Trp residues that were conserved in *L. lactis* lacto-N-biosidase (positions 236, 279, and 353). Multiple Trp residues are present in the C-terminal regions of the catalytic domains of all family 20 glycosyl hydrolases (Graham et al. J. Biol. Chem. 1988 263:16823-16829; Tews et al. Gene 1996 170:63-67). These Trp residues line the part of the substrate binding pocket that is complementary to the hydrophobic surfaces of the hexosamine sugar ring (Tews et al. Nature Struct. Biol. 1996 3:638-648). It is expected that mutation of amino acids in these regions of dispersin B and its orthologs will alter enzymatic activity.

In a preferred embodiment an isolated amino acid sequence of the present invention comprises SEQ ID NO:2, 4, 6, 8 or 10 or an active fragment or variants thereof. Preferred active fragments are those comprising a portion of the amino acid sequence of SEQ ID NO:2, 4, 6, 8 or 10 with similarities to the consensus sequence of the family 20 glycosyl hydrolase.

"Active variants" or "functionally equivalent variants" as used herein are polypeptide sequences structurally different from the dispersin B protein, but having no significant functional difference from the protein. For example, when orthologous polypeptide sequences from various strains of *A. actinomycetemcomitans* are aligned, divergence in amino acid sequence is observed, usually 0 to 10 percent (Kaplan et al. Oral Microbiol. Immunol. December 2002 17:354-359; Kaplan et al. Infect. Immun. 2001 69:5375-5384). Proteins displaying this amount of divergence are considered functionally equivalent variants because of the fact that mixing of genetic alleles that encode these variants is often observed in populations (Kaplan et al. Oral Microbol. Immunol. December 2002 17:354-359). The dispersin B sequence from *A. actinomycetemcomitans* strain IDH781 (SEQ ID NO:6), therefore, is expected to be a functionally equivalent or active variant of SEQ ID NO:2, and is included in the scope of the present invention. Similarly, dispersin B sequences from other strains of *A. actinomycetemcomitans*, such as those that exhibit different serotypes, restriction fragment length polymorphism genotypes, 16S ribosomal RNA genotypes, or arbitrarily-primed PCR genotypes that are commonly observed among phylogenetically diverse strains isolated from different subjects (Kaplan et al. J. Clin. Microbiol. 2002 40:1181-1187; Kaplan et al., Oral Microbiol. Immunol. December 2002 17:354-359), are also expected to be functionally equivalent or active variants of SEQ ID NO:2, and are included in the scope of the present invention.

Similarly, orthologous proteins from phylogenetically diverse species of bacteria are usually functionally equivalent or active variants, as evidenced by the fact that a common method for cloning genes of interest into plasmids is to screen a plasmid library for plasmids that complement a genetic mutation in a different species of bacteria (Kaplan et al. J. Mol. Biol. 1985 183:327-340). This is especially true of bacterial enzymes. Orthologous enzymes of different bacterial species can exhibit up to 50% divergence or greater, yet still utilize the identical substrate, catalyze the same chemical reaction, and produce the same product. This sequence divergence results from genetic drift coupled with fixation of selected genetic changes in the population. The genetic changes that are selected and fixed are those that alter characteristics of the enzyme other than substrate, reaction, and product, as for example, reaction rate, pH optimum, temperature optimum, level of expression, and interactions with other enzymes, such that these genetic changes confer upon a bacterial cell a selective advantage in its environment. Since *A. actinomycetemcomitans* is genetically closely related to *A. pleuropneumoniae* (Dewhirst et al. J. Bacteriol. 1992 174: 2002-2013) and produces a biofilm similar to that produced by *A. actinomycetemcomitans*, which as demonstrated herein detaches upon contact with *A. actinomycetemcomitans* dispersin B, it is expected that the *A. pleuropneumoniae* DspB homologue identified in SEQ ID NO:10 is a functionally equivalent or active variant of SEQ ID NO:2, and is included in the scope of the present invention. Similarly, since *Actinobacillus ligniersii* is genetically closely related to *Actinobacillus pleuropneumoniae* (Dewhirst et al. J. Bacteriol. 1992 174:2002-2013) and *Haemophilus aphrophilus* is genetically closely related to *A. actinomycetemcomitans* (Dewhirst et al. J. Bacteriol. 1992 174:2002-2013; Kaplan et al. J. Clin. Microbiol. 2002 40:1181-1187), and since both *A. ligniersii* and *Haemophilus aphrophilus* produce biofilms similar to that produced by *A. actinomycetemcomitans*, it is expected that the *Actinobacillus ligniersii* and *Haemophilus aphrophilus* dispersin homologues identified in SEQ ID NO:4 and SEQ ID NO:8, respectively, are functionally equivalent or active variants of SEQ ID NO:2, and are included in the scope of the present invention.

The above mentioned examples demonstrate functionally equivalent or active variants of *A. actinomycetemcomitans* dispersin B that occur in nature. As will be understood by those of skill in the art upon reading this disclosure, however, artificially produced genes that encode functionally equivalent or active variants of *A. actinomycetemcomitans* dispersin B can also be produced routinely in accordance with the teachings herein using various well known genetic engineering techniques. For example, a genetically engineered dispersin B enzyme that lacks 20 N-terminal amino acid residues, and also contained a 32 amino acid residue C-terminal tail, which if functionally equivalent to the natural dispersin B enzyme has been produced. It has also been shown that the methionine residue at the N-terminus of this genetically engineered dispersin B enzyme, when expressed in *E. coli*, was removed by the action of methionine aminopeptidase, yet the absence of the methionine did not affect enzyme activity. It has also been shown that cleavage of the C-terminal 28 amino acid residues from this genetically engineered dispersin B enzyme has no affect on enzyme activity. These examples demonstrate that artificial genes can be produced that encode functionally equivalent variants of *A. actinomycetemcomitans* dispersin B. These artificially produced functionally equivalent variants of *A. actinomycetemcomitans* dispersin B are included in the scope of the present invention.

The above mentioned examples demonstrate genetically-engineered, functionally equivalent variants of *A. actinomycetemcomitans* dispersin B that contain either a deletion of amino acid residues at the N-terminus of the protein, or the fusion of an additional polypeptide at the C-terminus of the protein. It is expected that other genetically-engineered alterations, such as the fusion of an additional polypeptide at the N-terminus of the protein, a deletion of amino acid residues at the C-terminus of the protein, internal deletions and insertions of amino acid residues, and amino acid substitutions, would also result in functionally equivalent variants of *A. actinomycetemcomitans* dispersin B. Information about which deletions, insertions, and amino acid substitutions would produce functionally equivalent variants of *A. actinomycetemcomitans* dispersin B can be obtained from amino acid sequence alignments, and from commonly available computer software that predicts polypeptide secondary structures based on both primary amino acid sequences and on amino acid sequence alignments with homologous proteins having known three-dimensional structures. A. actinomycetemcomitans dispersin B, for example, is a member of the family 20 glycosyl hydrolases, a family that includes several well-studied enzymes, and a family represented by numerous homologous primary amino acid sequences in the public databases. In some cases, three-dimensional structures of family 20 glycosyl hydrolases are known (Tews et al. Nature Struct. Biol. 1996 3:638-648). All family 20 glycosyl hydrolases exhibit a $(\beta\alpha)_8$-barrel motif (also known as a TIM-barrel motif; Tews et al. Nature Struct. Biol. 1996 3:638-648; Prag et al. J. Mol. Biol. 2000 300:611-617), which is by far the most common enzyme fold in the Protein Data Bank (PDB) database of known protein structures. It is estimated that 10% of all known enzymes have this domain (Wierenge, R. K., FEBS Lett. 2001 492:193-198). The $(\beta\alpha)_8$-barrel motif is seen in many different enzyme families, catalyzing completely unrelated reactions. The availability of numerous homologous primary amino acid sequences, combined with the availability of the three-dimensional structures of several A. actinomycetemcomitans dispersin B homologues, forms the basis of these sequence alignments and secondary structure predictions. For example, the $(\beta\alpha)_8$-barrel motif consists of eight α-helices and eight β-strands such that eight parallel β-strands form a barrel on the inside of the protein, which are covered by eight α-helices on the outside of the protein. Based on the above mentioned protein sequence alignments and structural predictions, it is expected that the eight β-strands in A. actinomycetemcomitans DspB comprise the amino acid residues surrounding positions 41-44, 69-81, 130-134, 169-171, 189-200, 253-256, 288-300, and 348-350 of SEQ ID NO:2. Any alteration in the amino acid sequence that disrupts the β-strand architecture of these eight regions would be expected to result in a decrease in enzyme activity because of a concomitant disruption in the three-dimensional structure of the $(\beta\alpha)_8$-barrel of the enzyme. Similarly, based on the above mentioned protein sequence alignments and structural predictions, it is expected that the eight α-helices in A. actinomycetemcomitans DspB comprise the amino acid residues surrounding positions 52-63, 89-93, 143-149, 176-183, 214-228, 269-284, 309-321, and 361-374 of SEQ ID NO:2. Any alteration in the amino acid sequence that disrupts the α-helical architecture of these eight regions would be expected to result in a decrease in enzyme activity because of a concomitant disruption in the three-dimensional structure of $(\beta\alpha)_8$-barrel of the enzyme. Similarly, because the β-strands consist of four inward pointing side chains (pointing into the β-barrel) and four outward pointing side chains (pointing towards the α-helices), it is expected that alterations in the inward-pointing amino acid residues will reduce enzyme activity because of concomitant alterations to the substrate binding pocket inside the $(\beta\alpha)_8$-barrel, and that alterations in the outward-pointing amino acid residues will reduce enzyme activity when they interfere with the interactions between the β-strands and the α-helices. Similarly, the active site of family 20 glycosyl hydrolases is always located at the C-terminal end of the eight parallel β-strands of the barrel. It is expected that alterations in the homologous region of A. actinomycetemcomitans dispersin B will affect enzyme activity. Similarly, it is predicted that the introduction of insertions and deletions into the regions between the α-helices and the β-strands, namely in positions 45-51, 64-68, 82-88, 94-129, 135-142, 150-168, 172-175, 182-188, 201-213, 229-252, 257-268, 285-287, 301-308, 322-347, and 351-360, in SEQ ID NO:2, will not effect enzyme activity. Similarly, it is expected that almost any alteration of residues 47 (Arginine), 203 (Aspartate) and 204 (Glutamate) will result in complete loss of enzyme activity, because these three residues have been shown to participate directly in substrate binding and catalysis in all family 20 glycosyl hydrolases (Mark et al. J. Biol. Chem. 1998 273: 19618-19624; Prag et al. J. Mol. Biol. 2000 300:611-617; Mark et al. J. Biol. Chem. 2001 276"10330-10337). Similarly, it is expected that alteration of the three tryptophan residues at positions 236, 257 and 350, to any non-aromatic amino acid residue will result in a decrease in enzyme activity because these three tryptophan residues have been shown to line part of the substrate-binding pocket that is complementary to the hydrophobic surfaces of the substrate hexosamine sugar ring (Tews et al. Nature Struct. Biol. 1996 3:638-648). As a result of the locations of these essential amino acid residues in A. actinomycetemcomitans dispersin B, it is predicted that no more than 46 amino acid residues can be deleted from the N-terminus, and no more that 31 amino acids can be deleted from the C-terminus, without loss of enzyme activity. All of these genetic alterations that result in functionally equivalent variants are included in the scope of the present invention.

Genes encoding functionally different variants of A. actinomycetemcomitans dispersin B can also be produced in accordance with the teachings of the instant application using well known genetic engineering techniques. For example, as mentioned above, it is expected that almost any alteration of residues 47 (Arginine), 203 (Aspartate) and 204 (Glutamate) in SEQ ID NO:2 will result in complete loss of enzyme activity. Alternatively, variants of A. actinomycetemcomitans dispersin B that exhibit characteristics that may be useful in a clinical setting could also be artificially produced. For example, the temperature optimum of A. actinomycetemcomitans dispersin B is 30° C. It may be desirable to produce a genetically-engineered variant of dispersin B that exhibits a temperature optimum of 37° C., thereby resulting in an increased effectiveness of the enzyme or decreased cost of treatment. Such variants can be artificially produced by first creating random mutations in the A. actinomycetemcomitans dspB gene sequence, for example by using UV light or a chemical mutagen like nitrosoguanidine, and then screening large numbers of these random variants, for example in a quantitative 96-well microtiter plate assay (Kaplan et al. J. Bacteriol. 2003 185:4693-4698), for ones that exhibit higher temperature optima. An alternative method is to utilize directed evolution of sequences by DNA shuffling (Christians et al. Nature Biotechnol. 1999 17:259-264; Dichek et al. J. Lipid Res. 1993 34:1393-1340), combined with a high-throughput robotic screen based upon a quantitative 96-well microtiter plate assay (Kaplan et al. J. Bacteriol. 2003 185: 4693-4698) to identify variants with increased temperature optima. The aforementioned methods can also be used to produce variants of A. actinomycetemcomitans dispersin B that exhibit increased substantivity to biomaterials, increased pH optima, increased stability in aqueous solutions, increased reaction rate, increased stability upon desiccation, and other characteristics that could result in increased effectiveness of the enzyme or decreased cost of treatment. An alternative method that can be used to produce useful variants is site-directed mutagenesis. For example, it is expected that the eight α-helices of the $(\beta\alpha)_8$-barrel in A. actinomycetemcomitans dispersin B contain many amino acid residues that are exposed on the outer surface of the enzyme, and that altering the outward-pointing amino acid residues of the eight α-helices will alter the outer surface properties of the enzyme, thereby potentially increasing the substantivity of the enzyme for biomaterials without affecting enzyme activity. Accordingly, these outward pointing amino acid residues can be systematically mutated, for example from polar residues to charged residues, and the resulting mutants screened to identify variants with increased substantivity to biomaterials. Functionally different variants of *A. actinomycetemcomitans* dispersin B that are intended to improve the clinical efficiency or cost effectiveness of the enzyme, when applied to detaching bacterial or fungal cells from biofilms, are included in the scope of the present invention.

Also provided in the present invention are fusion proteins and nucleic acid sequences encoding fusion proteins. Fusion proteins of the present invention comprise an amino acid sequence for an isolated soluble, N-acetylglucosaminidase protein which promotes detachment of bacterial cells from a biofilm and a second polypeptide. Exemplary second polypeptides of these fusion proteins include, but are not limited to, those which facilitate purification such as a His tag, those which facilitate attachment to a surface such as an antibody or a protein such as albumin, fibronectin or thrombin, and/or those which target the enzyme to the surface of bacterial or fungal cell such as a specific bacterial or fungal receptor. Nucleic acid sequences encoding such fusion proteins comprise an isolated nucleic acid sequence encoding soluble, β-N-acetylglucosaminidase or an active fragment or variant thereof which promotes detachment of bacterial or fungal cells from a biofilm and a second nucleic acid sequence encoding a second polypeptide. In a preferred embodiment, the second nucleic acid sequence encodes a polypeptide such as a His tag which facilitates purification, an antibody or protein such as albumin, fibronectin or thrombin which facilitates attachment of the fusion protein to a surface, or a bacterial or fungal receptor which specifically targets the fusion protein to the surface of a bacterial or fungal cell, respectively.

The dispersin B protein engineered to contain an octahistidine metal binding site at its C-terminus was expressed in *E. coli*. The protein was purified by Ni-affinity chromatography and the dispersin B portion was cleaved from the hybrid protein using thrombin. Analysis of the purified cleaved dispersin B protein by SDS-PAGE revealed the protein to migrate with an apparent molecular mass of 41 kDa. The N-terminal sequence of dispersin B was XCVKGNSIYPQK (SEQ ID NO:11) (where X is an unidentified residue). This matched codons 22 to 33 of CU1000 dspB, thus indicating that the dipeptide Met-Asn was cleaved from the N-terminus of the dispersin B fusion protein when expressed in *E. coli*. Analysis of purified, cleaved dispersin B protein by mass spectrophotometry resulted in a single major peak with an apparent molecular mass of 41.5 kDa, consistent with the predicted molecular mass of 41.4 kDa for the cleaved and processed dispersin B protein. The yield of dispersin B expressed in *E. coli* was 30 mg of protein per liter of culture.

The ability of dispersin B to cleave the glycosidic linkages of various 4-nitrophenyl-labeled synthetic hexosamine substrates was tested in an in vitro enzyme assay. Dispersin B showed specificity for the 1→4 glycosidic bond of β-substituted N-acetylglucosaminide, consistent with the known functions of other family 20 glycosyl hydrolases (Tews et al. Nature Struct. Biol. 1996 3:638-648). Dispersin B showed no activity against α-substituted N-acetylglucosaminide, or against α- or β-substituted N-acetylgalactosamine.

The glycosyl hydrolase activity of dispersin B was optimal at pH 5.0, which is similar to the pH optima of other family 20 glycosyl hydrolases. Dispersin B displayed maximum activity at 30° C. Dispersin B glycosyl hydrolase activity was inhibited by quinacrine (Kovacs, P. and Csaba, G. Cell Biochem. Funct. 2001 19:287-290) and NAG-thiazoline (Mark et al. J. Biol. Chem. 2001 276:10330-10337), two small molecule inhibitors of family 20 β-N-acetylglucosaminidases.

The effects of dispersin B protein on biofilm cell detachment of *A. actinomycetemcomitans* mutant strain JK1023 were then examined. In these experiments, dispersin B protein was added to growth medium of mutant strain JK1023 to determine if addition of this protein restored release of cells into the medium and dispersion. Polystyrene rods containing biofilm colonies of strain JK1023 were suspended in broth containing various amount of dispersin B, and the amount of biofilm cell detachment was measured by staining the bacteria growing on the bottom of the well with crystal violet. Purified dispersin B restored the ability of mutant strain JK1023 to release cells into the medium and colonize the bottom of the microtiter plate well in a dose-dependent manner. Heat-inactivated dispersin B had no effect on biofilm cell detachment of strain JK1023.

The effects of dispersin B protein on detachment of preformed biofilm colonies of *A. actinomycetemcomitans* and other bacteria were also examined. In these experiments, addition of dispersin B caused the detachment of preformed biofilm colonies of wild-type strain CU1000. Dispersin B (50 μg/ml) caused a 90% reduction in the amount of surface-associated bacteria after 6 hours. Further, analysis by light micrography showed that the surface of treated colonies became grainy and flocculent when compared to the smooth-textured biofilm colonies observed with mock-treated cells. Also, the surface of the culture vessel became covered with a similar grainy material which had a fibrous appearance under higher power. These findings are consistent with the observed reduction in adherence of preformed biofilm colonies treated with dispersin B.

Dispersin B caused a similar reduction in biofilm density when tested against biofilm colonies of four phylogenetically diverse strains of *A. actinomycetemcomitans* representing four different serotypes, a strain of the closely related bacterium *Haemophilus aphrophilus*, and two strains of the swine pathogen *Actinobacillus pleuropneumoniae*. Dispersin B did not cause the detachment of biofilm colonies of *Neisseria subflava*, *Cardiobacterium hominis* or *Streptococcus mitis*, bacteria which do not have biofilms comprising N-acetyl glucosamine residues.

Dispersin B also causes the detachment of *Staphylococcus epidermidis* from surfaces. The Gram-positive bacterium *S. epidermidis* is the most common cause of infection associated with catheters and other indwelling medical devices. *S. epidermidis* produces an extracellular slime composed of a polysaccharide containing primarily N-acetylglucosamine residues (Mack et al. J. Bacteriol. 1996 178:175; Baldassarri et al. Infect. Immun. 1996 64:3410) which enables it to form adherent films on plastic surfaces. Biofilm bacteria such as *S. epidermidis* are highly resistant to antibiotics and host defenses and nearly impossible to irradicate (Costerton et al. Annu. Rev. Microbiol. 1995 49:711). Thus, attachment of this bacteria to indwelling devices such as catheters can lead to osteomyelitis, acute sepsis and death, particularly in immunocompromised patients, and is a leading cause of nosocomial bloodstream and cardiovascular infections as well as morbidity in hospitalized patients (Vuong, C. and Otto, M. Microbes, Infect. 2002 4:481).

Four different strains of *S. epidermidis* isolated from infected intravenous catheters were used in these experiments. All four strains contained the ica genetic locus and produced dark red colonies on Congo red agar, both of which are indicative of slime production (Aricola et al. J. Clin. Microbiol. 2001 39:2151; Aricola et al. Biomaterials 2002

Biomaterials 23:4233). The ability of the four strains to form biofilms was measured by making serial dilutions of overnight cultures in fresh broth and then transferring the dilutions to the wells of a 96-well polystyrene microliter plate. After 16 hours of incubation, the wells were washed under running tap water to remove loosely adherent cells and the bacteria remaining attached to the bottoms of the well were stained with crystal violet. As expected all four strains produced adherent biofilms as indicated by the presence of dark-staining material on the bottoms of the wells. The amount of dark-staining material was quantitated by measuring its optical density at 590 nm in a microliter plate reader. When dispersin B protein was added to the wells 30 minutes prior to washing (final concentration, 40 μg/ml) little or no biofilm material was evident. In contrast, heat inactivated dispersin B protein had no effect on S. epidermidis biofilms. Two other N-acetylglucosaminidase enzymes that are homologous to A. actinomycetemcomitans dispersin B, Serratia marcescens chitinase and jack bean β-hexosaminidase, also had no effect on S. epidermidis biofilms. Unlike the orthologs described herein, these homologous proteins share less than 25% identity with dispersin B and do not exhibit biofilm-releasing activity. Thus, these experiments are demonstrative of dispersin B enzymatic activity being responsible for removing S. epidermidis biofilm cells from the surfaces of the wells. Dispersin B had no effect on viability of S. epidermidis cells.

The amount of dispersin B protein and the length of time needed to remove S. epidermidis biofilms from the microliter plate wells were also examined. In these experiments, multiple wells were inoculated with a $10^{-4}$ dilution of a S. epidermidis culture and the plate was incubated for 16 hours. After washing away loosely adherent cells, the wells were filled with phosphate buffered saline (PBS) and then various amounts of dispersin B protein (200 pg to 120 μg per ml final concentrations) were added to the wells for various lengths of time (0 to 9 minutes). Dispersin B treatment at a concentration of 4.8 μg/ml resulted in a decrease in absorbance to background levels (ca. 0.09 O.D. units) after 2 minutes. At a concentration of 40 ng/ml, dispersin B resulted in a greater than 50 percent reduction in optical density after 9 minutes (from 3.63 to 1.74 O.D. units). These data demonstrate that dispersin B causes detachment of S. epidermidis biofilms of clinically achievable concentrations of the enzyme.

Biofilm cell detachment was quantitated by growing S. epidermidis biofilms on polystyrene rods and then transferring the rods to tubes containing PBS (as a control) or PBS with 60 μg/ml of dispersin B. The tubes were incubated for 15 minutes, rinsed in PBS, and the bacteria remaining attached to the rods after treatment were removed by sonication and then quantitated by plating serial dilutions of the sonicates on agar. Mock-treated and dispersin B-treated rods were compared after staining with crystal violet. The mock-treated control rod contained a layer of dark-staining material corresponding to the thick biofilm that formed on its surface. The dispersin B-treated rod showed no trace of dark-staining material and was similar in appearance to a rod which was sonicated prior to staining and to an uninoculated rod. Quantitation of cells remaining attached to the rods revealed that dispersin B treatment resulted in a 5.8 log reduction in the number of surface-associated bacteria.

The ability of dispersin B to remove S. epidermidis biofilms grown attached to polyurethane and Teflon intravenous catheters was also examined. In these experiments, catheters were placed in tubes containing a $10^{-3}$ dilution of a S. epidermidis culture and incubated for 16 hours. The catheters were then rinsed with PBS and transferred to tubes containing PBS (as a control) or PBS with 60 μg/ml of dispersin B. After 5 minutes the catheters were rinsed with PBS and the biofilm bacteria remaining attached to the surface were stained with methylene blue (for polyurethane catheters) or crystal violet (for Teflon catheters). The control catheters contained a layer of dark-staining material on their surfaces indicating the presence of a biofilm, whereas the dispersin B-treated catheters contained no dark-staining material and were similar in appearance to uninoculated catheters.

Thus, dispersin B of the present invention is capable of removing S. epidermidis biofilms from various plastic biomaterials.

The ability of precoating surfaces with dispersin B to prevent S. epidermidis biofilm formation was also demonstrated. In these experiments, polyurethane and Teflon catheters in tubes containing PBS or PBS with 40 μg/ml of dispersin B were incubated at 4° C. for 24 hours. The catheters were then rinsed with PBS and transferred to tubes containing a $10^{-1}$ dilution of a S. epidermidis culture After 6 hours, the catheters were rinsed with PBS to remove loosely adherent cells and then stained as described supra. The surfaces of control catheters were covered with a layer of dark-staining material indicating the presence of a biofilm, whereas the surfaces of dispersin B-coated catheters contained no dark-staining material and were similar in appearance to uninoculated catheters. As shown, precoating plastic catheters with dispersin B of the present invention significantly reduced S. epidermidis attachment or biofilm formation. Catheters that were precoated for 10 minutes, and catheters that were precoated for 24 hours and then dried, were also resistant to colonization and biofilm formation by S. epidermidis.

Thus, as demonstrated by these experiments, addition of an isolated dispersin B protein as well as mutation of the dspB gene modulates the detachment of cells from biofilm colonies of various bacteria, particularly bacteria with a biofilm comprising a polysaccharide containing N-acetylglucosamine. Fungi also form biofilms of clinical significance which may compromise polysaccharide containing N-acetylglucosamine. It is believed that dispersin B will also be effective in degrading these fungal polysaccharides and modulating detachment of such fungal cells from their biofilms.

Accordingly, the present invention also relates to methods for modulating detachment of bacterial or fungal cells from biofilms, particularly bacteria or fungal with a biofilm comprising a polysaccharide containing N-acetylglucosamine.

By "modulating detachment" as used herein it is meant to be inclusive of increases as well as decreases in bacterial or fungal biofilm detachment or release of bacterial or fungal cells from the biofilm. Further, by "modulating detachment" it is also meant to be inclusive of changes in the ability of the bacteria or fungal to attach as a biofilm. For example, as demonstrated herein, dispersin B modulates detachment of S. epidermidis not only by promoting detachment but also by inhibiting the ability of the bacteria to attach to surfaces and form a biofilm.

In one embodiment of the present invention, the method comprises mutating dspB of bacterial cells to inhibit detachment of bacterial cells from biofilms such as in the JK1023 mutant of the present invention. In another embodiment, the method comprises decreasing expression and/or levels of soluble, β-N-acetylglucosaminidase or inhibiting activity of soluble, β-N-acetylglucosaminidase in bacterial cells so that detachment of bacterial cells is decreased.

The present invention also provides methods for promoting detachment of bacterial or fungal cells from a biofilm which comprises contacting bacterial or fungal cells with soluble, β-N-acetylglucosaminidase or an active fragment or variant thereof or a nucleic acid sequence encoding soluble, β-N- acetylglucosaminidase or an active fragment or variant thereof. For example, *A. actinomycetemcomitans* dispersin B was found to detach biofilms of *Haemophilus aphrophilus, Actinobacillus pleuropneumonaie* and *S. epidermidis*. It is believed that biofilm detachment of *Actinobacillus ligniersii*, as well as other bacteria or fungi with a biofilm comprising a polysaccharide containing N-acetylglucosamine including, but in no way limited to, *Staphylococcus aureus* and *Yersinia pestis* will also be promoted in the presence of soluble β-N-acetylglucosaminidase or an active fragment thereof of the present invention.

Accordingly, isolated dispersin B proteins and active fragments or variants thereof can be used to prevent or inhibit bacterial or fungal biofilm attachment and to treat infections by such bacteria or fungi.

In one embodiment, the isolated dispersin B protein or active fragment or variant thereof is used directly as a parenteral to treat biofilm infections such as mastitis in ewes, intramammary infections in cows or osteomyelitis and infective endocarditis in humans. In this embodiment, the isolated soluble, β-N-acetylglucosaminidase protein or active fragment or variant thereof is preferably administered as a pharmaceutical composition in a pharmaceutically acceptable carrier to an organism.

By "organism", as used herein it is meant to be inclusive of all animals including, but not limited to mammals, and most preferably humans.

Any pharmaceutically acceptable vehicle or carrier, as well as adjuvant, can be used in the manufacture, dissolution and administration of pharmaceutical preparations comprising dispersin B protein or active fragment or variant thereof. Such vehicles, carriers and adjuvants are well known to those of skill in the art and described in text books such as *Remington's Pharmaceutical Sciences*, Mack Publishing Co., Easton, Pa., 1985. Appropriate concentrations of active composition to be incorporated into pharmaceutical compositions can be routinely determined by those skilled in the art and is dependent upon the form of administration as well as the severity of the condition being treated.

Pharmaceutical formulations suitable for oral administration may be provided in convenient unit forms including, but not limited to, capsules or tablets, each containing a predetermined amount of the dispersin B protein or active fragment or variant thereof; as a powder or granules; as a solution, a suspension or as an emulsion. The dispersin B protein or active fragment or variant thereof can also be presented as a bolus, electuary, or paste. Tablets and capsules for oral administration may contain conventional excipients such as binding agents, fillers, lubricants, disintegrants, or wetting agents. The tablets may be coated according to methods well known in the art. Timed release formulations, which are known in the art, may also be suitable. Oral liquid preparations may be in the form of, for example, aqueous or oily suspensions, solutions, emulsions, syrups or elixirs, or may be presented as a dry product for constitution with water or other suitable vehicles before use. Such liquid preparations may contain conventional additives such as suspending agents, non-aqueous vehicles, including edible oils, or preservatives.

Dispersin B protein or active fragments or variants thereof of the present invention may also be formulated for parenteral administration, such as by injection, for example bolus injection or continuous infusion, and may be provided in unit dose form in ampules, pre-filled syringes, small volume infusion or in multi-dose containers with an added preservative. Pharmaceutically acceptable compositions comprising a dispersin B protein or active fragment or variant thereof for parenteral administration may be in the form of a suspension, solution or emulsion in oily or aqueous vehicles, and may contain formulatory agents such as suspending, stabilizing, and/or dispersing agents. Alternatively, the active ingredient may be in powder form, obtained by asceptic isolation of sterile solid or by lyophilization from solution, for constitution with a suitable vehicle such as sterile, pyrogen free water, before use.

For topical administration to the epidermis, dispersin B protein or an active fragment or variant thereof of the present invention may be formulated in an ointment, cream, or lotion, or as a transdermal patch. Ointments and creams, may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising dispersin B protein or an active fragment or variant thereof in a flavored base, usually sucrose and acacia or tragacanth; pastilles comprising the active ingredient in an inert base such as gelatin and glycerin or sucrose and acacia; and mouth washes comprising the active ingredient in a suitable liquid carrier. For topical administration to the eye, the dispersin B protein or active fragment or variant thereof can be made up in solution or suspension in a suitable sterile aqueous or non-aqueous vehicle. Additives such as buffers (e.g. sodium metabisulphite or disodium edeate) and thickening agents such as hypromellose can also be included.

For intra-nasal administration, dispersin B protein or an active fragment or variant thereof of the present invention can be provide in a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs.

For administration by inhalation, dispersin B protein or active fragment or variant thereof of the present invention can be delivered by insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the dispersin B protein or active fragment or variant thereof of the present invention can take the form of a dry powder composition, for example a powder mix of the active component and a suitable powder base such as lactose or starch. The powder composition may be presented in unit dosage form in, for example, capsules, cartridges or blister packs of gelatins, from which the powder can be administered with the aid of an inhalator or insufflator.

When desired, any of the above-described formulations may be adapted to provide sustained release of the dispersin B protein or active fragment or variant thereof.

The amount of dispersin B protein or active fragment or variant thereof of the present invention required for use in treatment will of course vary not only with the particular protein or active fragment or variant selected but also with the route of administration, the nature of the condition being treated, and the age and condition of the organism.

Increasing detachment of bacteria from a biofilm is also expected to decrease resistance of the bacteria to antibiotic therapy. Accordingly, the present invention also provide methods for enhancing efficacy of antibiotic therapy against bacterial infections by administration of a pharmaceutical composition of the present invention in combination with or prior to administration of an antibiotic.

In another embodiment of the present invention, wound dressings including but not limited to sponges or gauzes can be impregnated with the isolated dispersin B protein or active fragment or variant thereof to prevent or inhibit bacterial or fungal attachment and reduce the risk of wound infections. Similarly, catheter shields as well as other materials used to cover a catheter insertion sites can be coated or impregnated with a dispersin B protein or active fragment or variant thereof to inhibit bacterial or fungal biofilm attachment thereto. Adhesive drapes used to prevent wound infection during high risk surgeries can be impregnated with the isolated protein or active fragment or variant thereof as well. Additional medical devices which can be coated with a dispersin B protein or active fragment or variant thereof include, but are not limited, central venous catheters, intravascular catheters, urinary catheters, Hickman catheters, peritoneal dialysis catheters, endrotracheal catheters, mechanical heart valves, cardiac pacemakers, arteriovenous shunts, schleral buckles, prosthetic joints, tympanostomy tubes, tracheostomy tubes, voice prosthetics, penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, phosphate buffered saline (pH approximately 7.5) and bicarbonate buffer (pH approximately 9.0).

In yet another embodiment, an isolated dispersin B protein or active fragment or variant thereof can be incorporated in a liquid disinfecting solution. Such solutions may further comprise antimicrobials or antifungals such as alcohol, providone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws.

The nucleic acid and amino acid sequences of the present invention, as well as the mutant JK1023 strain can also be used to identify agents which modulate detachment of bacterial or fungal cells from biofilms. For example, the ability of an agent to modulate activity and/or expression of soluble, β-N-acetylglucosaminidase of the present invention can be assessed.

Examples of such agents include, but are not limited to antisense oligonucleotides or ribozymes targeted to the dspB gene, peptidomimetics of dispersin B, and small organic chemicals such as quinacrine and NAG-thiazoline which modulate dispersin B activity and/or levels and/or expression.

Agents which inhibit the ability of soluble, β-N-acetylglucosaminidase to promote detachment of bacterial cells from biofilms are expected to be useful in preventing the dissemination of infectious bacteria, particularly infectious bacteria of the oral cavity such as *A. actinomycetemcomitans* and closely related bacterium such as *Haemophilus aphrophilus*.

Agents which mimic dispersin B activity such as peptidomimetics and small organic molecules similar in structure and activity to dispersin B can be used in similar fashion to isolated dispersin B or an active fragment or variant thereof to prevent, inhibit or treat infection resulting from bacterial or fungal biofilm attachment to surfaces. Such uses are described herein in detail supra.

The present invention also provides primer pairs and kits comprising such primer pairs for use in identifying additional species of bacteria with dispersin B homologues. An exemplary degenerate primer pair useful in the kits of the present invention comprises 5'-GAYCAYGARAAYTAYCG-3' (SEQ ID NO:12) and 5'-TCNCCRTCRTARCTCCA-3' (SEQ ID NO:13), where Y is C or T, and R is A or G. Kits of the present invention preferably further comprise instructions for use of the kit and/or positive and negative control samples. Bacteria identified by these kits as having a dispersin B homologue can be further examined to determine if the homologue is an ortholog exhibiting the same or similar enzymatic activity as dispersin B. The primers and kits of the present invention are thus useful in identifying additional bacteria, biofilm attachment of which can be modulated using the nucleic acid sequences, amino acid sequences, and agents described herein as well as additional orthologous nucleic acid sequences and amino acid of dispersin B.

The following nonlimiting examples are provided to further illustrate the present invention.

EXAMPLES

Example 1

Bacterial Strains and Growth Conditions

*A. actinomycetemcomitans* CU1000 (serotype f) is a clinical strain isolated from a 13 year old patient with localized juvenile periodontitis (Fine et al. Microbiol. 1999 145:1335-1347). Strain CU1000N is a spontaneous nalidixic acid derivative of strain CU1000 that displays the same surface attachment, biofilm colony formation and biofilm dispersal phenotypes as the parental strain (Fine et al. Arch. Oral Biol. 2001 46:1065-1078; Kachlany et al. J. Bacteriol. 2000 182: 6169-6176; Kachlany et al. Mol. Microbiol. 2001 40:542-554; Thomson et al. J. Bacteriol. 1999 181:7298-7307). Mutagenesis of strain CU1000N with transposon IS903φkan was carried in accordance with the procedures set forth by Thomson et al. (J. Bacteriol. 1999 181:7298-7307). Other strains utilized include *A. actinomycetemcomitans* DF2200 (serotype a), NJ8800 (serotype b), NJ2700 (serotype c), and NJ9500 (serotype e) (Kaplan et al. J. Clin. Microbiol. 2002 40:1181-1187); and *A. actinomycetemcomitans* strain IDH781 (Saarela et al. Oral Microbiol. Immunol. 1993 8:111-115); *Haemophilus aphrophilus* NJ8700 (Kaplan et al. J. Clin. Microbiol. 2002 40:1181-1187); *Neisseria subflava* NJ9702 (Kaplan, J. B. and Fine, D. H. Appl. Environ. Microbiol. 2002 68:4943-4950); *Cardiobacterium hominis* NJ6500; *Actinobacillus ligniersii* strain 19393 (obtained from ATCC, Manassa, Va.); and *Streptococcus mitis* NJ9705 (Kaplan, J. B. and Fine, D. H. Appl. Environ. Microbiol. 2002 68:4943-4950). *S. epidermidis* strains were isolated from the surfaces of infected intravenous catheters and were identified by using the Api-Staph biochemical identification kit (Biomérieux, Lyons France). *A. pleuropneumoniae* strains were obtained from the Veterinary Diagnostics Laboratory (Iowa State University, Ames, Ill.). Bacteria were grown in Trypticase soy broth (BD Biosystems) supplemented with 6 grams of yeast extract and 8 grams of glucose/liter. Inoculated culture vessels were incubated at 37° C. in 10% $CO_2$, except for *S. epidermidis* cultures, which were incubated at 37° C. in air.

Example 2

Cloning and Sequencing dspB

The transposon insertion site in *A. actinomycetemcomitans* mutant strain JK1023 was cloned and sequenced by using an inverse PCR method in accordance with Kaplan et al. (Infect. Immun. 2001 69:5375-5384). The DNA sequence of the inverse PCR product was compared to the genome sequence of *A. actinomycetemcomitans strain HK*1651 from the *Actinobacillus* Genome Sequencing Project and the transposon was found to have inserted into a long open reading frame (ORF) which was designated dspB. Primers that hybridize to sequences upstream and downstream from HK1651 dspB were used to amplify by PCR the dspB coding region from *A. actinomycetemcomitans* strain CU1000 using methods in accordance with Kaplan et al. (Infect. Immun. 2001 69:5375-5384). The forward primer (5-GCGCGC CATatgAATTGTTGCGTAAAAGGCAATTCC-3 (SEQ ID NO:14)) introduced an NdeI restriction site (underlined) and an ATG initiation codon (lower case) at codon positions 19 to 20 of dspB, and the reverse primer (5-GC GGTACCCTCATCCCCATTCGTCTTATGAATC-3 (SEQ ID NO:15)) replaced the dspB stop codon with a KpnI restriction site (underlined). The PCR product (1,106 bp) was digested with NdeI and KpnI and ligated into the NdeI/KpnI sites of plasmid pET29b (Novagen). The insert of the resulting plasmid (designated pRC1) was subjected to DNA sequence analysis in accordance with procedures described by Kaplan et al. (Infect. Immun. 2001 69:5375-5384).

Example 3

Expression and Purification of Recombinant

Dispersin B protein

Plasmid pRC1 carries a gene that encoded amino acids 21 to 381 of dspB fused to a 32 amino acid residue C-terminal tail containing an hexahistidine metal-binding site and a thrombin protease cleavage site which could be used to cleave the C-terminal tail from the hybrid protein. This gene was located downstream from an isopropyl-$\beta$-D-thiogalactopyranoside (IPTG)-inducible tac promoter.

Expression of DspB in *E. coli*

A one liter Erlenmeyer flask containing 500 ml of LB broth supplemented with 50 μg/ml of kanamycin was inoculated with 5 ml of an overnight culture of *E. coli* strain BL21(DE3) (Dubendorff, J. W. and Studier, F. W. J. Mol. Biol. 1991 219:61-68) transformed with pRC1. The flask was incubated at 37° C. with agitation (200 rpm) until the optical density of the culture (measured at 280 nm) reached 0.6 (approximately 3 hours). IPTG was added to a final concentration of 0.2 mM and the flask was incubated for an additional 5 hours with agitation. The cells were harvested by centrifugation for 15 minutes at 6,000×g and the cell pellet was stored at −80° C.

Protein Purification

The cell pellet was thawed on ice and resuspended in 20 ml of lysis buffer [20 mM Tris-HCl (pH 7.2), 0.1% sodium dodecyl sulfate] containing 10 mg/ml lysozyme. The cell suspension was sonicated for 30 seconds at 50% capacity, 70% duty cycle in a Branson model 4550 sonicator equipped with a microprobe and then cooled on ice for 30 seconds. The sonication and cooling steps were repeated four additional times. The cells were pelleted by centrifugation as above and the supernatant was transferred to a new tube. The cell pellet was resuspended in 20 ml of lysis buffer without lysozyme and five additional cycles of sonication and cooling were performed. The cells were pelleted by centrifugation and the supernatant was removed and transferred to a new tube. The two supernatants were combined and loaded onto a 3 ml bed volume Ni-affinity column (catalog no. 154-0990, Pharmacia) according to the instructions supplied by the manufacturer. The column was washed with 50 ml of wash buffer [50 mM MOPS (pH 8.5), 20 mM KCl] containing 5 mM imidazole, followed by 25 ml of wash buffer containing 50 mM imidazole and 25 ml of wash buffer containing 100 mM imidazole. Fractions (1.5 ml each) were collected during the final wash and assayed for the presence of the hybrid protein by SDS polyacrylamide gel electrophoresis (SDS-PAGE) and Coomassie blue staining in accordance with procedures described by Sambrook et al. (1989. Molecular cloning: a laboratory manual, 2nd ed. Cold Spring Harbor Laboratory Press, Cold Spring Harbor, N.Y.). Fractions containing the protein were pooled and dialyzed overnight against water using a 10,000 MW cut-off dialysis membrane. The purified protein was digested with 5 units of thrombin (Novagen) per mg of protein for 1 hour at room temperature and the thrombin was removed using a Thrombin Cleavage Capture Kit (Novagen) according to instructions supplied with the kit. Undigested protein was removed by loading the sample onto a Ni-affinity column as described above and washing the column with 10 ml of wash buffer containing 5 mM imidazole. Fractions of the wash (1.5 ml each) were collected and analyzed for the presence of the protein by SDS-PAGE. Fractions containing the protein were pooled, dialyzed against water, and stored at −20° C. N-terminal sequence analysis of the purified protein was carried out using the Edman degradation procedure on a Beckman model 2300 protein sequencer. Mass spectra were determined by using a Hitachi model 4414 mass spectrometer.

Example 4

Enzyme Assays

Synthetic substrates (purchased from Sigma Chemical Co.) were 4-nitrophenyl-N-acetyl-$\beta$-D-galactosaminide, 4-nitrophenyl-N-acetyl-$\alpha$-D-galactosaminide, 4-nitrophenyl-N-acetyl-$\beta$-D-glucosaminide, and 4-nitrophenyl-N-acetyl-$\alpha$-D-glucosaminide. Enzyme reactions were carried out in a 10 ml volume containing 50 mM sodium phosphate buffer (pH 5.9), 100 mM NaCl, 5 mM substrate, and 3.7 Mg/ml purified protein in a 15 ml polypropylene tube placed in a 37° C. water bath. The reaction was terminated at various times by transferring 1 ml of the reaction mixture to a new tube containing 5 μl NaOH. The increase in absorption resulting from the release of p-nitrophenolate in each tube was measured in a Shimadzu UV-Mini spectrophotometer set to 405 nm.

Example 5

Identification of dspB Orthologues in Other Strains of *A. actinomycetemcomitans* and in Other Species of Bacteria The microbial genome database www.ncbi.nlm.nih.gov was searched for homologues of *A. actinomycetemcomitans* dspB. dspB homologues were identified in the unfinished genomes of *A. pleuropneumoniae* serovars 1, 5 and 7. The *A. pleuropneumoniae* dspB homologues displayed approximately 60% identity at the amino acid level with the *A. actinomycetemcomitans* CU1000 DspB sequences. Additional searching was performed for DspB homologues in other members of the Pasteurellaceae family. The amino acid sequence of *A. actinomycetemcomitans* CU1000 DspB was aligned with the *A. pleuropneumoniae* DspB homologues and two regions of the sequence were identified that were highly conserved. Degenerate oligonucleotide primers were then synthesized that hybridized to DNA sequences encoding these conserved amino acids (5'-GAYCAYGARAAY-TAYCG-3' (SEQ ID NO:12) and 5'-TCNCCRTCRT-ARCTCCA-3' (SEQ ID NO:13), where Y=C or T, R=A or G, and N=A or C or G or T) and these primers were used to amplify by PCR genomic DNAs purified from various species of Pasteurellaceae. A PCR product of the expected size was observed in genomic DNA from *A. actinomycetemcomitans* strain IDH781 (Saarela et al. 1993. Oral Microbiol. Immunol. 8:111-115), *A. pleuropneumoniae* strain IA5 (obtained from the Veterinary Diagnostics Laboratory, Iowa State University, Ames, Iowa), *Haemophilus aphrophilus* strain NJ8700 (Kaplan et al. 2002 J. Clin. Microbiol. 40:1181-1187), and *A. ligniersii* strain 19393 (obtained from the American Type Culture Collection, Manassas, Va.). No PCR product was observed with DNA from *Haemophilus somnus, Actinobacillus equuli, Pasteurella multocida*, and *Mannheimia haemolytica*.

The PCR products were cloned into multicopy plasmids and subjected to DNA sequence analysis. FIG. 1 shows a comparison of the predicted DspB amino acid sequence of *A. actinomycetemcomitans* CU1000 DspB and the sequences of the DspB homologues from the other strain of *A. actinomycetemcomitans* and other Pasteurellaceae bacteria.

Example 6

Overexpression of dspB in a Wild-Type Strain of *A. actinomycetemcomitans*

In order to determine the effects of overexpressing dspB in a wild-type strain of *A. actinomycetemcomitans*, a plasmid was constructed which contains dspB under the control of an isopropyl-β-D-thiogalactopyranoside (IPTG)-inducible promoter. This plasmid was introduced into wild-type strain CU1000, and the cells were grown in the presence of 1 mM IPTG. CU1000 cells harboring the dspB expressing plasmid exhibited a smooth-colony morphology on agar and produced biofilm colonies in broth that displayed a hyper-dispersing phenotype, as indicated by the presence of increased numbers of satellite colonies on the surface of the culture vessel. These findings confirm that dspB expression parallels the amount of biofilm dispersal.

Example 7

Detachment of Biofilm Cells from Polystyrene Rods in Microtiter Plates

An assay to measure the detachment of cells from preformed biofilm colonies grown on polystyrene rods was carried out in 96-well microtiter plates. Biofilm colonies were grown on polystyrene rods suspended in broth in the 96-wells of a microtiter plate. Cells that detached from the biofilm fell to the bottom of the well where they attached to the surface and formed new biofilm colonies. The amount of biofilm growth on the bottom of the well, which was proportional to the Number of cells that detached from the biofilm colonies on the rods, was measured by staining with crystal violet. The detachment assay was carried out as follows.

Construction of the Apparatus

The lid of a 96-well polystyrene flat-bottomed tissue culture plate (Falcon No. 353072) was modified as follows: First, 96 1.5-mm diameter holes were drilled in the lid, with each hole in a position corresponding to the center of one of the 96 wells. Then, an 11-mm long polystyrene rod (1.5-mm diameter, Plastruct Corp., City of Industry, Calif.) was placed in each hole (with one end of the rod flush against the top of the lid) and secured with trichloromethane plastic solvent. When this modified lid was placed on a 96-well microtiter plate bottom, the rods were suspended in the wells with the bottom of each rod approximately 2 mm above the bottom of the well. The modified lid was sterilized by soaking in 70% ethanol for 30 minutes and air drying in a biological safety cabinet.

Inoculation and Incubation of Polystyrene Rods

The microtiter plate bottom was filled with medium (100 μl per well) and each well was inoculated with a single 2-3 day old colony from an agar plate using a sterile toothpick. The modified lid was then placed on the inoculated plate to submerge the polystyrene rods in the inoculated medium, and the plate was incubated at 37° C. for 24 hours to allow that bacteria to adhere to the rods. The lid was then transferred to a fresh microtiter plate containing prewarmed medium and incubated for an additional 24 hours to allow biofilm cells to detach from the rods.

Measuring Detached Cells

The lid was removed and the plate was washed extensively under running tap water to remove loosely adherent cells. The wells were filled with 100 μl of Gram-staining reagent (2 grams crystal violet, 0.8 grams ammonium oxalate, 20 ml ethanol per 100 ml) and the plate was incubated at room temperature for 10 minutes. The plate was re-washed extensively under running tap water to remove unbound dye. The wells were than filled with 100 μl of ethanol and the plate was incubated at room temperature for 10 minutes to solubilize the dye. The optical density (at 590 nm) of the ethanol/dye solution in each well was measured using a Bio-Rad benchmark microplate reader.

Example 8

Growth of Biofilms on Polystyrene Rods

Polystyrene rods (1.5 mm diam; Plastruct Corp., City of Industry, Calif.) were cut into 35 mm lengths, sterilized in 70% ethanol for 30 minutes, and air dried in a biological safety cabinet. Rods were placed into 1.5 ml microcentrifuge tubes containing 0.5 ml of broth inoculated with *S. epidermidis* and incubated for 16 hours. Rods were then rinsed under running tap water and then placed in fresh microcentrifuge tubes containing 0.5 ml of PBS or PBS plus dispersin B. Rods were rinsed with water and stained with crystal violet as previously described (Kaplan, J. B., and Fine, D. H. Appl. Environ. Microbiol. 2002 68:4943-4950). For sonication, rods were placed in 15 ml conical centrifuge tubes containing 3 ml of PBS at then sonicated for 30 seconds at 40% duty cycle and 70% capacity in Branson model 200 sonicator equipped with a cup horn. For quantitation of detached cells, sonicates were serially diluted and plated on medium solidified with 1.5% agar.

Example 9

Growth of Biofilms in Polystyrene Microtiter Plates

The wells of a 96-well polystyrene microtiter plate (model 3595, Corning) were filled with 100 ml of broth inoculated with *S. epidermidis* and the plate was incubated for 16 hours. Microtiter plates were washed by aspirating the medium and washing the well three times with 200 ml of PBS, or by submerging the entire plate in a tub of cold, running tap water. Biofilms were stained with crystal violet as previously described (Kaplan, J. B., and Fine, D. H. Appl. Environ. Microbiol. 2002 68:4943-4950).

Example 10

96-Well Microtiter Plate Biofilm Cell Detachment Assay

The wells of a 96-well microtiter plate (Falcon no. 353072) were filled with 100 µl of medium containing 102 to $10^4$ CFU of bacteria and incubated at 37° C. in 10% $CO_2$ for 20 hours. Ten µl of enzyme solution [1 mg $ml^{-1}$ in phosphate buffered saline (PBS)], or 10 µl of PBS in the case of controls, was added to each well and the plates were incubated for an additional 6 hours. The wells were washed extensively under running tap water and the bacteria remaining attached to the surface were stained with crystal violet, rewashed, and destained with ethanol in accordance with procedures described by Kachlany et al. Mol. Microbiol. 2001 40:542-554). The optical density (O.D.) of the ethanol-dye solution was measured in a BioRad Benchmark microtiter plate reader set to 590 nm.

Example 11

Growth of Biofilms on Intravenous Catheters

Polyurethane catheters (1.1 mm diam, model 381434, Becton-Dickinson) and Teflon catheters (1.2 mm diam, model 3055, Critikon) were employed. The tips of the catheters were plugged with sterile high vacuum grease to prevent media and dye from entering the lumen. Catheters were inoculated and treated as described above for polystyrene rods. Precoating of catheters with dispersin B was carried out in PBS or in sodium phosphate buffer (pH 9) for 10 minutes to 24 hours. In some cases, coated catheters were air dried for 24 hours before use. Teflon catheters were stained with crystal violet as previously described (Kaplan, J. B., and Fine, D. H. Appl. Environ. Microbiol. 2002 68:4943-4950). Polyurethane catheters were stained with 1% methylene blue in water for 2 minutes.

What is claimed is:

1. A wound dressing comprising an external surface coated or impregnated with a DispersinB (DspB) polypeptide encoded by a nucleic acid sequence of at least 95% sequence identity to nucleotides 61 to 1143 of SEQ ID NO:1, wherein the DspB polypeptide cleaves β-substituted N-acetylglucosaminide.

2. The wound dressing of claim 1, wherein the wound dressing is a sponge, gauze, adhesive drape or catheter shield.

3. A transdermal patch comprising an external surface coated or impregnated with a DispersinB (DspB) polypeptide encoded by a nucleic acid sequence of at least 95% sequence identity to nucleotides 61 to 1143 of SEQ ID NO:1, wherein the DspB polypeptide cleaves β-substituted N-acetylglucosaminide.

4. The wound dressing of claim 1, wherein the DspB polypeptide is SEQ ID NO:2.

5. The transdermal patch of claim 3, wherein the DspB polypeptide is SEQ ID NO:2.

6. The wound dressing of claim 1, further comprising a second polypeptide fused to the DspB polypeptide.

7. The wound dressing of claim 6, wherein the second polypeptide is thrombin or fibronectin.

8. The wound dressing of claim 4, further comprising a second polypeptide fused to the DspB polypeptide.

9. The wound dressing of claim 8, wherein the second polypeptide is thrombin or fibronectin.

10. The transdermal patch of claim 3, further comprising a second polypeptide fused to the DspB polypeptide.

11. The transdermal patch of claim 10, wherein the second polypeptide is thrombin or fibronectin.

12. The transdermal patch of claim 5, further comprising a second polypeptide fused to the DspB polypeptide.

13. The transdermal patch of claim 12, wherein the second polypeptide is thrombin or fibronectin.

* * * * *

SEQUENCE LISTING

<160> NUMBER OF SEQ ID NOS: 15

<210> SEQ ID NO 1
<211> LENGTH: 1146
<212> TYPE: DNA
<213> ORGANISM: Actinobacillus actinomycetemcomitans strain CU1000N

<400> SEQUENCE: 1

```
atgaattata ttaagaaaat tattttatct cttttcctac tgggactatt tagcgtgttg      60
aattgttgcg taaaaggcaa ttccatatat ccgcaaaaaa caagtaccaa gcagaccgga     120
ttaatgctgg acatcgcccg acattttat tcacccgagg tgattaaatc ctttattgat     180
accatcagcc tttccggcgg taattttctg cacctgcatt tttccgacca tgaaaactat     240
gcgatagaaa gccatttact taatcaacgt gcggaaaatg ccgtgcaggg caaagacggt     300
atttatatta atccttatac cggaaagcca ttcttgagtt atcggcaact tgacgatatc     360
aaagcctatg ctaaggcaaa aggcattgag ttgattcccg aacttgacag cccgaatcac     420
atgacggcga tctttaaact ggtgcaaaaa gacagagggg tcaagtacct tcaaggatta     480
aaatcacgcc aggtagatga tgaaattgat attactaatg ctgacagtat tactttatg      540 caatctttaa tgagtgaggt tattgatatt tttggcgaca cgagtcagca ttttcatatt     600
ggtggcgatg aatttggtta ttctgtggaa agtaatcatg agtttattac gtatgccaat     660
aaactatcct acttttaga gaaaaagg ttgaaaaccc gaatgtggaa tgacggatta       720
attaaaaata cttttgagca aatcaaccg aatattgaaa ttacttattg gagctatgat     780
ggcgatacgc aggacaaaaa tgaagctgcc gagcgccgtg atatgcgggt cagtttgccg     840
gagttgctgg cgaaaggctt tactgtcctg aactataatt cctattatct ttacattgtt     900
ccgaaagctt caccaacctt ctcgcaagat gccgcctttg ccgccaaaga tgttataaaa     960
aattgggatc ttggtgtttg ggatggacga aacaccaaaa accgcgtaca aaatactcat    1020
gaaatagccg gcgcagcatt atcgatctgg ggagaagatg caaaagcgct gaaagacgaa    1080
acaattcaga aaaacacgaa aagtttattg gaagcggtga ttcataagac gaatggggat    1140
``` gagtga 1146

<210> SEQ ID NO 2
<211> LENGTH: 381
<212> TYPE: PRT
<213> ORGANISM: Actinobacillus actinomycetemcomitans strain CU1000N

<400> SEQUENCE: 2

```
Met Asn Tyr Ile Lys Lys Ile Ile Leu Ser Leu Phe Leu Leu Gly Leu
1               5                   10                  15

Phe Ser Val Leu Asn Cys Cys Val Lys Gly Asn Ser Ile Tyr Pro Gln
            20                  25                  30

Lys Thr Ser Thr Lys Gln Thr Gly Leu Met Leu Asp Ile Ala Arg His
        35                  40                  45

Phe Tyr Ser Pro Glu Val Ile Lys Ser Phe Ile Asp Thr Ile Ser Leu
    50                  55                  60

Ser Gly Gly Asn Phe Leu His Leu His Phe Ser Asp His Glu Asn Tyr
65                  70                  75                  80

Ala Ile Glu Ser His Leu Leu Asn Gln Arg Ala Glu Asn Ala Val Gln
                85                  90                  95

Gly Lys Asp Gly Ile Tyr Ile Asn Pro Tyr Thr Gly Lys Pro Phe Leu
            100                 105                 110

Ser Tyr Arg Gln Leu Asp Asp Ile Lys Ala Tyr Ala Lys Ala Lys Gly
        115                 120                 125

Ile Glu Leu Ile Pro Glu Leu Asp Ser Pro Asn His Met Thr Ala Ile
    130                 135                 140

Phe Lys Leu Val Gln Lys Asp Arg Gly Val Lys Tyr Leu Gln Gly Leu
145                 150                 155                 160

Lys Ser Arg Gln Val Asp Asp Glu Ile Asp Ile Thr Asn Ala Asp Ser
                165                 170                 175

Ile Thr Phe Met Gln Ser Leu Met Ser Glu Val Ile Asp Ile Phe Gly
            180                 185                 190

Asp Thr Ser Gln His Phe His Ile Gly Gly Asp Glu Phe Gly Tyr Ser
        195                 200                 205

Val Glu Ser Asn His Glu Phe Ile Thr Tyr Ala Asn Lys Leu Ser Tyr
    210                 215                 220

Phe Leu Glu Lys Lys Gly Leu Lys Thr Arg Met Trp Asn Asp Gly Leu
225                 230                 235                 240

Ile Lys Asn Thr Phe Glu Gln Ile Asn Pro Asn Ile Glu Ile Thr Tyr
                245                 250                 255

Trp Ser Tyr Asp Gly Asp Thr Gln Asp Lys Asn Glu Ala Ala Glu Arg
            260                 265                 270

Arg Asp Met Arg Val Ser Leu Pro Glu Leu Leu Ala Lys Gly Phe Thr
        275                 280                 285

Val Leu Asn Tyr Asn Ser Tyr Tyr Leu Tyr Ile Val Pro Lys Ala Ser
    290                 295                 300

Pro Thr Phe Ser Gln Asp Ala Ala Phe Ala Ala Lys Asp Val Ile Lys
305                 310                 315                 320

Asn Trp Asp Leu Gly Val Trp Asp Gly Arg Asn Thr Lys Asn Arg Val
                325                 330                 335

Gln Asn Thr His Glu Ile Ala Gly Ala Ala Leu Ser Ile Trp Gly Glu
            340                 345                 350

Asp Ala Lys Ala Leu Lys Asp Glu Thr Ile Gln Lys Asn Thr Lys Ser
        355                 360                 365
```

Leu Leu Glu Ala Val Ile His Lys Thr Asn Gly Asp Glu
    370                 375                 380

<210> SEQ ID NO 3
<211> LENGTH: 555
<212> TYPE: DNA
<213> ORGANISM: Actinobacillus ligniersii strain 19393

<400> SEQUENCE: 3
gatcacgaga attatgcatt ggaaagttct tatttggaac aacgagaaga aaatgccgtt      60
gagaaaaacg gaacctattt caatccgaaa acaaataagc cgtttctcac ttataaacag     120
ctcaatgaaa ttatctatta tgccaaagaa cgaaatattg aaattgtgcc tgaagtcgat     180
agcccgaatc atatgacggc gatttttgat cttttaaccc ttaagcacgg taaggagtat     240
gtgaaagggc tgaaatcgcc ttatcttgcc gaggaaatcg atattaataa ccctgaagcg     300
gttgaaatta tcaaaacctt aatcggtgaa gtgatttata tttttgggca ttccagccga     360
cactttcata tcggcggaga cgaatttagt tatgcggtcg aaaacaatca cgaatttatt     420
cgttatgtaa atacgctaaa tgactttatt aataacaaag gactaattac ccgtatttgg     480
aacgacggtt tgattaaaaa caatttaaat gagcttaatc ggaatatcga aattactt     540 tggagctacg acggt                                                      555

<210> SEQ ID NO 4
<211> LENGTH: 185
<212> TYPE: PRT
<213> ORGANISM: Actinobacillus ligniersii strain 19393

<400> SEQUENCE: 4

Asp His Glu Asn Tyr Ala Leu Glu Ser Ser Tyr Leu Glu Gln Arg Glu
1               5                   10                  15

Glu Asn Ala Val Glu Lys Asn Gly Thr Tyr Phe Asn Pro Lys Thr Asn
            20                  25                  30

Lys Pro Phe Leu Thr Tyr Lys Gln Leu Asn Glu Ile Ile Tyr Tyr Ala
        35                  40                  45

Lys Glu Arg Asn Ile Glu Ile Val Pro Glu Val Asp Ser Pro Asn His
    50                  55                  60

Met Thr Ala Ile Phe Asp Leu Leu Thr Leu Lys His Gly Lys Glu Tyr
65                  70                  75                  80

Val Lys Gly Leu Lys Ser Pro Tyr Leu Ala Glu Glu Ile Asp Ile Asn
                85                  90                  95

Asn Pro Glu Ala Val Glu Ile Ile Lys Thr Leu Ile Gly Glu Val Ile
            100                 105                 110

Tyr Ile Phe Gly His Ser Ser Arg His Phe His Ile Gly Gly Asp Glu
        115                 120                 125

Phe Ser Tyr Ala Val Glu Asn Asn His Glu Phe Ile Arg Tyr Val Asn
    130                 135                 140

Thr Leu Asn Asp Phe Ile Asn Asn Lys Gly Leu Ile Thr Arg Ile Trp
145                 150                 155                 160

Asn Asp Gly Leu Ile Lys Asn Asn Leu Asn Glu Leu Asn Arg Asn Ile
                165                 170                 175

Glu Ile Thr Tyr Trp Ser Tyr Asp Gly
            180                 185

<210> SEQ ID NO 5
<211> LENGTH: 558
<212> TYPE: DNA

<213> ORGANISM: Actinobacillus actinomycetemcomitans strain IDH781

<400> SEQUENCE: 5

| | | |
|---|---|---|
| gatcatgaaa actatgcgat agaaagccat ttacttaatc aacgtgcgga aaatgccgta | 60 |
| cagggcaaag acggtattta tattaatcct tataccggaa agccattctt gagttatcga | 120 |
| caacttgacg atatcaaagc ctatgctaag gcaaaaggca ttgagttgat tcccgaactt | 180 |
| gatagtccga atcacatgac ggcgatcttt aaactggtgc aaaaagacag agggatcaag | 240 |
| tatcttcaag gattaaaatc acgccaggta gatgatgaaa ttgatattac taatgctgac | 300 |
| agtattgctt ttatgcaatc tttaatgagt gaggttattg atattttttgg cgacacgagt | 360 |
| cagcattttc atattggtgg cgatgaattt ggttattctg tggaaagtaa tcatgagttt | 420 |
| attacgtatg ccaataaact atcctacttt ttagagaaaa aggggttgaa acccgaatg | 480 |
| tggaatgacg gattaattaa aagtactttt gagcaaatca acccgaatat tgaaattact | 540 |
| tattggagct atgatggc | 558 |

<210> SEQ ID NO 6
<211> LENGTH: 186
<212> TYPE: PRT
<213> ORGANISM: Actinobacillus actinomycetemcomitans strain IDH781

<400> SEQUENCE: 6

Asp His Glu Asn Tyr Ala Ile Glu Ser His Leu Leu Asn Gln Arg Ala
1               5                  10                  15

Glu Asn Ala Val Gln Gly Lys Asp Gly Ile Tyr Ile Asn Pro Tyr Thr
            20                  25                  30

Gly Lys Pro Phe Leu Ser Tyr Arg Gln Leu Asp Asp Ile Lys Ala Tyr
        35                  40                  45

Ala Lys Ala Lys Gly Ile Glu Leu Ile Pro Glu Leu Asp Ser Pro Asn
    50                  55                  60

His Met Thr Ala Ile Phe Lys Leu Val Gln Lys Asp Arg Gly Ile Lys
65                  70                  75                  80

Tyr Leu Gln Gly Leu Lys Ser Arg Gln Val Asp Asp Glu Ile Asp Ile
                85                  90                  95

Thr Asn Ala Asp Ser Ile Ala Phe Met Gln Ser Leu Met Ser Glu Val
            100                 105                 110

Ile Asp Ile Phe Gly Asp Thr Ser Gln His Phe His Ile Gly Gly Asp
        115                 120                 125

Glu Phe Gly Tyr Ser Val Glu Ser Asn His Glu Phe Ile Thr Tyr Ala
    130                 135                 140

Asn Lys Leu Ser Tyr Phe Leu Glu Lys Lys Gly Leu Lys Thr Arg Met
145                 150                 155                 160

Trp Asn Asp Gly Leu Ile Lys Ser Thr Phe Glu Gln Ile Asn Pro Asn
                165                 170                 175

Ile Glu Ile Thr Tyr Trp Ser Tyr Asp Gly
            180                 185

<210> SEQ ID NO 7
<211> LENGTH: 558
<212> TYPE: DNA
<213> ORGANISM: Haemophilus aphrophilus strain NJ8700

<400> SEQUENCE: 7

| | | |
|---|---|---|
| gaccacgaaa attatgcttt agaaagcagg ttgttgaatc agcgggcaga aaacgcaatt | 60 |
| ttaaataaaa acggaattta tattaatcct tacaccaata agcctttctt gagttatcaa | 120 |

-continued

```
cagttggatg acattaaagc atatgcaaaa ttaaaaggta ttgagcttat tcccgaatta      180
gatagcccga atcacatgac agcgattttt accttattaa aaaagaaaa aggaaaaaat      240 tatcttcaat cgttaaaatc accacaaaat gatgaggaaa ttagcattac caatccggac     300
agcattgcat ttatgcaatc cttattaaca gaggtaattc ataccttggg cgatagcacc    360
aagcattttc atattggcgg agatgagttt ggttatgatg aaaatagtaa tcatgaattt     420
attacctatg ccaataaatt ggctgatttt ttaagagaaa aaggattaaa aactcgaatt    480
tggaatgatg gtttaattaa aaataccata gatcaattaa atcctaatat tgaaattacc    540
tactggagtt acgacggc                                                  558
```

<210> SEQ ID NO 8
<211> LENGTH: 186
<212> TYPE: PRT
<213> ORGANISM: Haemophilus aphrophilus strain NJ8700

<400> SEQUENCE: 8

```
Asp His Glu Asn Tyr Ala Leu Glu Ser Arg Leu Leu Asn Gln Arg Ala
1               5                   10                  15

Glu Asn Ala Ile Leu Asn Lys Asn Gly Ile Tyr Ile Asn Pro Tyr Thr
            20                  25                  30

Asn Lys Pro Phe Leu Ser Tyr Gln Gln Leu Asp Asp Ile Lys Ala Tyr
        35                  40                  45

Ala Lys Leu Lys Gly Ile Glu Leu Ile Pro Glu Leu Asp Ser Pro Asn
    50                  55                  60

His Met Thr Ala Ile Phe Thr Leu Leu Lys Lys Glu Lys Gly Lys Asn
65                  70                  75                  80

Tyr Leu Gln Ser Leu Lys Ser Pro Gln Asn Asp Glu Glu Ile Ser Ile
                85                  90                  95

Thr Asn Pro Asp Ser Ile Ala Phe Met Gln Ser Leu Leu Thr Glu Val
            100                 105                 110

Ile His Thr Phe Gly Asp Ser Thr Lys His Phe His Ile Gly Gly Asp
        115                 120                 125

Glu Phe Gly Tyr Asp Glu Asn Ser Asn His Glu Phe Ile Thr Tyr Ala
    130                 135                 140

Asn Lys Leu Ala Asp Phe Leu Arg Glu Lys Gly Leu Lys Thr Arg Ile
145                 150                 155                 160

Trp Asn Asp Gly Leu Ile Lys Asn Thr Ile Asp Gln Leu Asn Pro Asn
                165                 170                 175

Ile Glu Ile Thr Tyr Trp Ser Tyr Asp Gly
            180                 185
```

<210> SEQ ID NO 9
<211> LENGTH: 555
<212> TYPE: DNA
<213> ORGANISM: Actinobacillus pleuropneumoniae strain IA5

<400> SEQUENCE: 9

```
gatcacgaga attatgcatt ggaaagttct tatttggaac aacgagaaga aaatgcgacc     60
gagaaaaacg gaacctattt caatccgaaa acaaataagc cgtttctcac ttataaacag     120
ctcaatgaaa ttatctatta tgccaaagaa cgaaatattg aaattgtgcc tgaagtcgat     180
agcccgaatc atatgacggc gatttttgat cttttaaccc ttaagcacgg aaaggaatac    240 gtaaagggc taaaatcgcc ttatatcgcc gaggaaatcg atattaataa ccccgaagcg     300
```

```
gttgaagtta ttaaaacctt aatcggtgaa gtgatctata ttttcggaca ttcaagccgg    360
catttccata tcggcggaga tgaatttagc tatgcggtcg aaaataatca tgaatttatt    420
cggtatgtga ataccttaaa tgattttatc aattccaaag ggctaattac ccgtgtttgg    480
aatgacggtt tgatcaaaaa caacttaagc gaactcaata aaaacattga aatcacttac    540
tggagctacg acggt                                                     555
```

```
<210> SEQ ID NO 10
<211> LENGTH: 185
<212> TYPE: PRT
<213> ORGANISM: Actinobacillus pleuropneumoniae strain IA5

<400> SEQUENCE: 10
```

Asp His Glu Asn Tyr Ala Leu Glu Ser Ser Tyr Leu Glu Gln Arg Glu
1               5                   10                  15

Glu Asn Ala Thr Glu Lys Asn Gly Thr Tyr Phe Asn Pro Lys Thr Asn
            20                  25                  30

Lys Pro Phe Leu Thr Tyr Lys Gln Leu Asn Glu Ile Ile Tyr Tyr Ala
        35                  40                  45

Lys Glu Arg Asn Ile Glu Ile Val Pro Glu Val Asp Ser Pro Asn His
    50                  55                  60

Met Thr Ala Ile Phe Asp Leu Leu Thr Leu Lys His Gly Lys Glu Tyr
65                  70                  75                  80

Val Lys Gly Leu Lys Ser Pro Tyr Ile Ala Glu Ile Asp Ile Asn
                85                  90                  95

Asn Pro Glu Ala Val Glu Val Ile Lys Thr Leu Ile Gly Glu Val Ile
            100                 105                 110

Tyr Ile Phe Gly His Ser Ser Arg His Phe His Ile Gly Gly Asp Glu
        115                 120                 125

Phe Ser Tyr Ala Val Glu Asn Asn His Glu Phe Ile Arg Tyr Val Asn
    130                 135                 140

Thr Leu Asn Asp Phe Ile Asn Ser Lys Gly Leu Ile Thr Arg Val Trp
145                 150                 155                 160

Asn Asp Gly Leu Ile Lys Asn Asn Leu Ser Glu Leu Asn Lys Asn Ile
                165                 170                 175

Glu Ile Thr Tyr Trp Ser Tyr Asp Gly
            180                 185

```
<210> SEQ ID NO 11
<211> LENGTH: 12
<212> TYPE: PRT
<213> ORGANISM: A. actinomycetemcomitans
<220> FEATURE:
<221> NAME/KEY: MISC_FEATURE
<222> LOCATION: (1)..(1)
<223> OTHER INFORMATION: X=any amino acid

<400> SEQUENCE: 11
```

Xaa Cys Val Lys Gly Asn Ser Ile Tyr Pro Gln Lys
1               5                   10

```
<210> SEQ ID NO 12
<211> LENGTH: 17
<212> TYPE: DNA
<213> ORGANISM: Artificial sequence
<220> FEATURE:
<223> OTHER INFORMATION: Synthetic

<400> SEQUENCE: 12
```

```
gaycaygara aytaycg                                                    17

<210> SEQ ID NO 13
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n=a, c, g or t

<400> SEQUENCE: 13
tcnccrtcrt arctcca                                                    17

<210> SEQ ID NO 14
<211> LENGTH: 36
<212> TYPE: DNA
<213> ORGANISM: Artificial sequence
<220> FEATURE:
<223> OTHER INFORMATION: Synthetic

<400> SEQUENCE: 14
gcgcgccata tgaattgttg cgtaaaaggc aattcc                               36

<210> SEQ ID NO 15
<211> LENGTH: 33
<212> TYPE: DNA
<213> ORGANISM: Artificial sequence
<220> FEATURE:
<223> OTHER INFORMATION: Synthetic

<400> SEQUENCE: 15
gcggtaccct catcccatt cgtcttatga atc                                   33
```